US008571245B2

(12) United States Patent
Takagi et al.

(10) Patent No.: US 8,571,245 B2
(45) Date of Patent: Oct. 29, 2013

(54) HEARING ASSISTANCE SUITABILITY DETERMINING DEVICE, HEARING ASSISTANCE ADJUSTMENT SYSTEM, AND HEARING ASSISTANCE SUITABILITY DETERMINING METHOD

(75) Inventors: Yoshiaki Takagi, Kanagawa (JP); Gempo Ito, Kanagawa (JP); Eiji Noguchi, Kanagawa (JP); Takashi Katayama, Kanagawa (JP); Hikaru Takato, Miyagi (JP)

(73) Assignee: Panasonic Corporation, Osaka (JP)

( * ) Notice: Subject to any disclaimer, the term of this patent is extended or adjusted under 35 U.S.C. 154(b) by 275 days.

(21) Appl. No.: 13/059,288

(22) PCT Filed: Jun. 15, 2010

(86) PCT No.: PCT/JP2010/003947
§ 371 (c)(1),
(2), (4) Date: Feb. 28, 2011

(87) PCT Pub. No.: WO2010/146825
PCT Pub. Date: Dec. 23, 2010

(65) Prior Publication Data
US 2011/0142272 A1 Jun. 16, 2011

(30) Foreign Application Priority Data

Jun. 16, 2009 (JP) .................................. 2009-143735
Apr. 15, 2010 (JP) .................................. 2010-094485

(51) Int. Cl.
*H04R 25/00* (2006.01)

(52) U.S. Cl.
USPC ........................................................ 381/321

(58) Field of Classification Search
USPC ........... 381/60, 23.1, 312, 328, 330; 181/130; 73/1.82, 585, 645, 646; 600/25, 559; 700/94

See application file for complete search history.

(56) References Cited

U.S. PATENT DOCUMENTS

| 8,094,848 B1 * | 1/2012 | Frerking et al. ............... 381/315 |
| 8,130,989 B2 * | 3/2012 | Latzel ............................ 381/314 |

(Continued)

FOREIGN PATENT DOCUMENTS

| JP | 2003-501986 | 1/2003 |
| JP | 2003-244794 | 8/2003 |

(Continued)

OTHER PUBLICATIONS

International Search Report issued Sep. 28, 2010 in corresponding International Application No. PCT/JP2010/003947.

(Continued)

*Primary Examiner* — Curtis Kuntz
*Assistant Examiner* — David J Ho
(74) *Attorney, Agent, or Firm* — Wenderoth, Lind & Ponack, L.L.P.

(57) ABSTRACT

A hearing assistance suitability determining device (120) according to the present invention is a hearing assistance suitability determining device (120) which determines a suitability (153) of a subject for dichotic hearing assistance, and includes: a hearing ability information obtaining unit (130) which obtains left-ear hearing ability information (150) and right-ear hearing ability information (151) each of which indicates a hearing ability for frequencies; a hearing ability type determining unit (131) which determines, among hearing ability types each of which is defined by a tendency in a change of the hearing ability with respect to the frequencies, a hearing ability type (152) of the hearing ability indicated by the left-ear hearing ability information (150) and the right-ear hearing ability information (151); and a suitability deciding unit (132) which determines, with reference to a suitability database (144), the suitability (153) of the subject for the dichotic hearing assistance based on a suitability corresponding, in the suitability database (144), to the hearing ability type (152) determined by the hearing ability type determining unit (131), the suitability database (144) showing a correspondence relationship between each of the hearing ability types and one of suitabilities of the subject for dichotic hearing assistance.

13 Claims, 27 Drawing Sheets

(56) References Cited

U.S. PATENT DOCUMENTS

| | | |
|---|---|---|
| 2004/0015099 A1 | 1/2004 | Nakaichi et al. |
| 2008/0082327 A1 | 4/2008 | Murase et al. |
| 2008/0260190 A1* | 10/2008 | Kidmose .................. 381/314 |
| 2010/0046777 A1 | 2/2010 | Ito et al. |
| 2010/0183161 A1* | 7/2010 | Boretzki .................... 381/60 |
| 2010/0234757 A1* | 9/2010 | Stromsted .................. 600/559 |
| 2010/0257128 A1* | 10/2010 | De Vries et al. ............ 706/12 |

FOREIGN PATENT DOCUMENTS

| | | |
|---|---|---|
| JP | 2004-121338 | 4/2004 |
| JP | 2006-87018 | 3/2006 |
| WO | 00/78096 | 12/2000 |

OTHER PUBLICATIONS

Megumi Takahashi et al. "The effects of auditory characteristics to the dichotic listening hearing aid processing", The Acoustical Society of Japan (ASJ), vol. 35, No. 3, Apr. 22, 2005, pp. 203-208 (with English abstract).

Y. Suzuki et al., "Determination of filtering parameters for dichotic-listening binaural hearing aids", Acoustics '08, Jun. 2008, pp. 1153-1158.

* cited by examiner

FIG. 3

| Frequency | Hearing level | |
|---|---|---|
| | Left ear | Right ear |
| 125 Hz | 30 dB | 40 dB |
| 250 Hz | 30 dB | 40 dB |
| 500 Hz | 40 dB | 45 dB |
| 1000 Hz | 50 dB | 60 dB |
| 2000 Hz | 55 dB | 50 dB |
| 4000 Hz | 60 dB | 55 dB |
| 8000 Hz | 65 dB | 50 dB |

| i | Hearing ability type | Probability for effectiveness $\alpha$ | Amount of expected improvement $\beta$ |
|---|---|---|---|
| 1 | High-frequency sloping type | 73 % | +6.7 % |
| 2 | High-frequency plunging type | 0 % | -2 % |
| 3 | Flat type | 67 % | +5.0 % |
| 4 | Chevron type | 33 % | +3.3 % |

| # | Subject | Hearing level (dB) 125 | 250 | 500 | 1K | 2K | 4K | 8K | Effect of dichotic hearing assistance 800 | 1250 | 2000 | Hearing ability for assigned band (dB) Left high tone | Right high tone | Determination result | Clinical result 800 | 1250 | 2000 | Consistency 800 | 1250 | 2000 |
|---|---|---|---|---|---|---|---|---|---|---|---|---|---|---|---|---|---|---|---|---|
| 1 | Right ear | 30 | 30 | 25 | 40 | 55 | 65 | 85 | -10% | -5% | -3% | 80 | 90 | L | L | L | L | O | O | O |
| 1 | Left ear | 35 | 35 | 25 | 45 | 50 | 60 | 65 | 1% | 8% | -3% | | | | | | | | | |
| 2 | Right ear | 30 | 35 | 30 | 40 | 60 | 65 | 85 | 8% | 4% | 2% | 95 | 90 | R | R | L | R | O | X | O |
| 2 | Left ear | 30 | 35 | 30 | 40 | 60 | 65 | 70 | 1% | 5% | 0% | | | | | | | | | |
| 3 | Right ear | 60 | 55 | 40 | 35 | 25 | 55 | 50 | 1% | 5% | 4% | 75 | 70 | R | R | R | R | O | O | O |
| 3 | Left ear | 45 | 45 | 35 | 40 | 20 | 55 | 50 | -6% | -1% | 1% | | | | | | | | | |
| 4 | Right ear | 40 | 40 | 45 | 60 | 50 | 55 | 65 | 13% | -6% | 6% | 95 | 80 | R | R | R | R | O | X | O |
| 4 | Left ear | 30 | 30 | 40 | 50 | 55 | 60 | 50 | -1% | -8% | -1% | | | | | | | | | |
| 5 | Right ear | 25 | 35 | 55 | 40 | 40 | 40 | 60 | -4% | -1% | 1% | 80 | 75 | R | L | R | R | X | O | O |
| 5 | Left ear | 25 | 35 | 50 | 45 | 45 | 50 | 65 | 5% | -4% | 5% | | | | | | | | | |
| 6 | Right ear | 30 | 35 | 30 | 30 | 55 | 65 | 95 | -3% | -1% | -3% | 90 | 80 | R | R | R | R | O | O | O |
| 6 | Left ear | 20 | 25 | 30 | 35 | 55 | 60 | 70 | 7% | 8% | 4% | | | | | | | | | |
| 7 | Right ear | 20 | 20 | 20 | 30 | 45 | 65 | 70 | 1% | 5% | 2% | 75 | 65 | L | L | L | L | O | O | O |
| 7 | Left ear | 15 | 20 | 20 | 45 | 55 | 60 | 75 | -5% | -3% | -4% | | | | | | | | | |
| 8 | Right ear | 25 | 25 | 15 | 20 | 50 | 65 | 70 | 5% | 3% | 0% | 75 | 80 | L | L | R | R | O | O | X |
| 8 | Left ear | 20 | 25 | 40 | 50 | 55 | 60 | 75 | 0% | 6% | -3% | | | | | | | | | |
| 9 | Right ear | 25 | 35 | 40 | 30 | 55 | 55 | 55 | 0% | 2% | -4% | 90 | 95 | R | L | R | R | O | X | O |
| 9 | Left ear | 35 | 40 | 40 | 50 | 55 | 55 | 55 | 10% | 7% | 0% | | | | | | | | | |
| 10 | Right ear | 40 | 50 | 50 | 55 | 65 | 65 | 70 | 17% | 14% | 4% | 105 | 110 | R | R | R | R | X | O | O |
| 10 | Left ear | 30 | 45 | 60 | 60 | 55 | 60 | 55 | 5% | 12% | 7% | | | | | | | | | |
| 11 | Right ear | 20 | 25 | 40 | 45 | 50 | 60 | 65 | 5% | 12% | 7% | 85 | 75 | L | R | R | L | O | O | X |
| 11 | Left ear | 25 | 25 | 40 | 55 | 60 | 60 | 70 | -7% | -5% | -14% | | | | | | | | | |
| 12 | Right ear | 20 | 15 | 20 | 40 | 45 | 50 | 70 | 2% | 5% | -3% | 65 | 60 | R | L | L | L | X | X | O |
| 12 | Left ear | 10 | 15 | 25 | 50 | 50 | 55 | 55 | 6% | 17% | 6% | | | | | | | | | |
| 13 | Right ear | 30 | 35 | 35 | 45 | 55 | 55 | 55 | 2% | -3% | -8% | 90 | 95 | L | L | R | L | O | O | O |
| 13 | Left ear | 35 | 40 | 40 | 50 | 60 | 55 | 60 | 7% | 0% | 2% | | | | | | | | | |
| 14 | Right ear | 40 | 45 | 50 | 55 | 60 | 55 | 60 | 7% | 0% | -4% | 105 | 105 | L | L | L | L | O | O | O |
| 14 | Left ear | 40 | 45 | 40 | 55 | 60 | 60 | 60 | 0% | 4% | -4% | | | | | | | | | |
| 15 | Right ear | 25 | 20 | 35 | 50 | 55 | 60 | 65 | 2% | 2% | 2% | 75 | 75 | L | L | L | L | O | O | O |
| 15 | Left ear | 20 | 20 | 35 | 45 | 60 | 55 | 60 | -1% | 4% | 9% | | | | | | | | | |
| 16 | Right ear | 45 | 50 | 40 | 45 | 50 | 55 | 60 | 5% | 0% | 9% | 100 | 95 | R | L | L | R | X | X | O |
| 16 | Left ear | 40 | 40 | 30 | 35 | 50 | 60 | 65 | 6% | 5% | 0% | | | | | | | | | |

HEARING ASSISTANCE SUITABILITY DETERMINING DEVICE, HEARING ASSISTANCE ADJUSTMENT SYSTEM, AND HEARING ASSISTANCE SUITABILITY DETERMINING METHOD

TECHNICAL FIELD

The present invention relates to hearing assistance suitability determining devices, hearing assistance adjustment systems, and hearing assistance suitability determining methods, and particularly to a hearing assistance suitability determining device which determines a suitability of a subject for dichotic hearing assistance.

BACKGROUND ART

In recent years, the aging of population has progressed, and there has been a growing number of hearing-impaired people due to aging. In order to maintain the quality of life of the elderly, it is important for them to be able to hear sounds that they cannot hear as they grow older, especially words. Thus, it is considered that the need for hearing aids will increase more and more.

On one hand, a deterioration in hearing of the hearing-impaired people differs from person to person. Accordingly, when a hearing-impaired person directly wears an off-the-rack hearing aid, the hearing aid is not suitable for the specific hearing impairment of such a person. In other words, it is necessary to measure aural characteristics of buyers when selling hearing aids, and to set each of the hearing aids according to a symptom of a corresponding one of the buyers.

In the currently most common aural characteristics test, a pure tone is produced by using an audiometer, and the minimum sound pressure level (hearing level) at which subjects can hear is measured. Generally, the lowest audibility level (hereinafter, referred to as a hearing level) is measured for the respective sinusoidal waves (pure tones) of 125 Hz, 250 Hz, 500 Hz, 1000 Hz, 2000 Hz, 4000 Hz, and 8000 Hz. In addition, if necessary, the same measurement may be performed for the respective sinusoidal waves of 750 Hz, 1500 Hz, 3000 Hz, and 6000 Hz. A unit of hearing level is dB (decibel). A sound pressure level at which people having a normal hearing ability can hear is 0 dB, a hearing ability diminishes as a value of a hearing level increases. A graph on which a hearing level at each of frequencies is plotted is called an audiogram, and is widely used to set the hearing aids. FIG. 1 shows an example of an audiogram.

FIG. 2 is a block diagram showing a common hearing assistance adjustment system 900. The hearing assistance adjustment system 900 shown in FIG. 2 causes a hearing-impaired person to hear, through headphones, a pure tone produced by an audiometer 901. Then, a measuring person operates the audiometer 901 when the hearing-impaired person hears the tone for measurement, so as to measure a hearing level of the hearing-impaired person.

After the audiometer 901 completes the measurement of the hearing level, in a hearing assistance adjustment device 901, a hearing level obtaining unit 911 obtains a hearing level at each of frequencies measured by the audiometer 901, as shown in FIG. 3. Next, an amplification amount calculating unit 912 calculates, based on the obtained hearing level at each frequency, an amplification amount for compensating a deterioration in hearing of the hearing-impaired person.

An amplification amount display unit 913 notifies a person in charge of adjustment of the calculated amplification amount. Furthermore, a hearing aid setting unit 914 sets the calculated amplification amount to an internal parameter of a hearing aid 903.

The adjustment of the hearing aid 903 for compensation (amplification) according to a hearing level of an individual is completed through the above procedure.

Moreover, Patent Literature 1 has proposed, in conventional hearing assistance adjustment processing, a method for substituting an amplification amount setting process having specific patterns for an amplification amount setting process which is performed in detail for each frequency, by classifying a general shape shown in audiograms into some predetermined values and combining the predetermined values with an overall hearing level.

On the other hand, it is said that frequency resolution of the hearing-impaired people has been reduced in addition to reduced hearing sensitivity. Here, the frequency resolution is a subject's ability to differentiate between two tones having different frequencies. Normal-hearing people can differentiate between two tones having adjacent frequencies such as 1 kHz and 1.2 kHz. However, the hearing-impaired people whose frequency resolution has been reduced cannot differentiate between the two tones.

Furthermore, in recent years, a model in which auditory filters are used has been proposed as a model for representing a frequency-analysis mechanism for human auditory. This model represents the frequency-analysis mechanism for human inner ears with an aggregate of band filters (auditory filters) which divide the mechanism into frequency bands. When a width of an auditory filter is large, it is considered that frequency resolution has been reduced.

Large reduction in the frequency resolution grows an influence of masking between frequency band components, particularly masking high-frequency components by low-frequency components (upward masking). Especially in speech, a vowel having a main component in low frequencies has a large amount of energy. The vowel having the large amount of energy masks a consonant having a main component in high frequencies. This causes a problem such as reduction in ability to hear words or significant reduction in speech discrimination ability in noise.

The problem caused by the deterioration in frequency resolution is a phenomenon based on a principle different from the reduced hearing sensitivity. Therefore, amplification of sound by the hearing aids cannot solve the problem, and the problem has been a major hurdle for the hearing-impaired people in terms of the hearing of words.

Examples of hearing assistance processing which is intended to increase clarity of audio input signals by reducing the masking between frequency bands include dichotic hearing assistance with which an input signal is divided on the frequency axis to be assigned to respective left and right ears. Past study examples have proposed, in the dichotic hearing assistance, a method for dividing an input audio signal by a frequency in a region where auditory filters are placed, and assigning an audio signal having a frequency lower than a crossover frequency to one of the ears and an audio signal having a frequency higher than the crossover frequency to the other ear. It has been reported that this method can increase clarity of speech (Non Patent Literature 1). FIG. 4 shows a structure for deciding setting of the hearing assistance method. In FIG. 4, an auditory filter measuring unit 951 measures an auditory filter. Moreover, it is decided by which frequency a tone region is divided into a high-tone region and a low-tone region, according to a value obtained by a frequency resolution calculating unit 952. Patent Literature 2 has proposed a speeding-up method concerning the auditory filter measuring unit 951.

Nevertheless, it has been reported that the dichotic hearing assistance cannot increase the clarity for all of the hearing-impaired people, and did not produce an effect on some hearing-impaired people (Non Patent Literature 1). Thus, when the dichotic hearing assistance is applied to hearing aids, it is necessary to determine whether or not to recommend the dichotic hearing assistance to a hearing-impaired person for whom adjustment of the hearing aids is made. However, measuring an auditory filter using the above method allows only prediction of a part of a setting value of the dichotic hearing assistance. In other words, currently there is no established method as a suitability determining method for the dichotic hearing assistance.

CITATION LIST

Patent Literature

[PTL 1]
Japanese Unexamined Patent Application Publication No. 2003-501986
[PTL 2]
Japanese Unexamined Patent Application Publication No. 2024421338
[Non Patent Literature]
[NPT 1]
Y. Suzuki et al. "Determination of filtering parameters for dichotic-listening binaural hearing aids", Acoustic 08 Paris, (France), 2008

SUMMARY OF INVENTION

Technical Problem

Traditionally, measuring by audiometer has not been sufficient to determine a suitability of dichotic hearing assistance, and there has been a need for separately measuring frequency resolution of a hearing ability of a user. However, there has been a problem that it takes a time to measure the frequency resolution, and thus it is unrealistic to measure it at a clinical site.

The present invention has been devised to solve the conventional problem, and has an object to provide a hearing assistance suitability determining device which makes it possible to readily determine a suitability of a subject for dichotic hearing assistance.

Solution to Problem

In order to solve the above problem, a hearing assistance suitability determining device according to an aspect of the present invention is a hearing assistance suitability determining device which determines a suitability of a subject for dichotic hearing assistance, and includes: a hearing ability information obtaining unit configured to obtain hearing ability information indicating a hearing ability of the subject for frequencies; a hearing ability type determining unit configured to determine, among hearing ability types each of which is defined by a tendency in a change of the hearing ability with respect to the frequencies, a hearing ability type of the hearing ability indicated by the hearing ability information; and a suitability deciding unit configured to decide, with reference to a table, the suitability of the subject for the dichotic hearing assistance based on a suitability corresponding, in the table, to the hearing ability type determined by the hearing ability type determining unit, the table showing a correspondence relationship between each of the hearing ability types and one of suitabilities for dichotic hearing assistance.

With this structure, the hearing assistance suitability determining device according to the aspect of the present invention makes it possible to determine whether or not the dichotic hearing assistance is suitable for the subject based only on the hearing ability information of the subject. In this way, the hearing assistance suitability determining device according to the aspect of the present invention easily determines the suitability of the subject for the dichotic hearing assistance.

Furthermore, one of the hearing ability types is a high-frequency sloping type in which a hearing ability decreases as a frequency becomes higher, and the suitability deciding unit may be configured to decide that the suitability of the subject for the dichotic hearing assistance when the hearing ability type determined by the hearing ability type determining unit is the high-frequency sloping type is to be higher than the suitability when the hearing ability type determined by the hearing ability type determining unit is not the high-frequency sloping type.

Moreover, one of the hearing ability types is a high-frequency plunging type, the hearing ability type determining unit may be configured to determine that the hearing ability type of the hearing ability is the high-frequency plunging type, when a decrement of the hearing ability in a frequency range higher than a predetermined frequency is greater than a predetermined first threshold, and the suitability deciding unit may be configured to decide that the suitability of the subject for the dichotic hearing assistance when the hearing ability type determined by the hearing ability type determining unit is the high-frequency plunging type is to be lower than the suitability when the hearing ability type determined by the hearing ability type determining unit is the high-frequency sloping type.

Furthermore, one of the hearing ability types is a flat type, the hearing ability type determining unit may be configured to determine that the hearing ability type of the hearing ability is the flat type, when an amount of change of the hearing ability in all the frequencies indicated by the hearing ability information is smaller than a predetermined second threshold, and the suitability deciding unit may be configured to decide that the suitability of the subject for the dichotic hearing assistance when the hearing ability type determined by the hearing ability type determining unit is the flat type is to be lower than the suitability when the hearing ability type determined by the hearing ability type determining unit is the high-frequency sloping type, and is to be higher than the suitability when the hearing ability type determined by the hearing ability type determining unit is the high-frequency plunging type.

Moreover, one of the hearing ability types is a chevron type in which the hearing ability increases and then decreases as the frequency becomes higher, and the suitability deciding unit may be configured to decide that the suitability of the subject for the dichotic hearing assistance when the hearing ability type determined by the hearing ability type determining unit is the chevron type is to be lower than the suitability when the hearing ability type determined by the hearing ability type determining unit is the high-frequency sloping type, is to be higher than the suitability when the hearing ability type determined by the hearing ability type determining unit is the high-frequency plunging type, and is to be lower than the suitability when the hearing ability type determined by the hearing ability type determining unit is the flat type.

Furthermore, the hearing ability type determining unit may be configured to determine a rate indicating a probability that the hearing ability type of the hearing ability indicated by the hearing ability information corresponds to each of the hearing ability types, and the suitability deciding unit may be configured to calculate a multiplication value for each hearing ability type by multiplying a suitability corresponding to a hearing ability type in the table by a rate corresponding to the hearing ability type determined by the hearing ability type determining unit, and to calculate the suitability of the subject for the dichotic hearing assistance by adding up the calculated multiplication values.

With these structures, the hearing assistance suitability determining device according to the aspect of the present invention makes it possible to determine whether or not the dichotic hearing assistance is suitable for even a subject whose auditory characteristics are difficult to be classified into a hearing type, based only on the hearing ability information of the subject.

Moreover, the hearing ability information obtaining unit may be configured to obtain, as the hearing ability information, left-ear hearing ability information which indicates a left-ear hearing ability of the subject for frequencies and right-ear hearing ability information which indicates a right-ear hearing ability of the subject for frequencies, and the hearing assistance suitability determining device may further include: a hearing ability calculating unit configured to calculate a left-ear high tone hearing ability and a left-ear low tone hearing ability in the left-ear hearing ability information, and a right-ear high tone hearing ability and a right-ear high tone hearing ability in the right-ear hearing ability information, the left-ear high tone hearing ability being a hearing ability in a frequency range higher than a predetermined crossover frequency, the left-ear low tone hearing ability being a hearing ability in a frequency range lower than the crossover frequency, the right-ear high tone hearing ability being a hearing ability in the frequency range higher than the crossover frequency, and the right-ear low tone hearing ability being a hearing ability in the frequency range lower than the crossover frequency; a first adding unit configured to calculate a right-high-tone hearing ability by adding up the right-ear high tone hearing ability and the left-ear low tone hearing ability; a second adding unit configured to calculate a left-high-tone hearing ability by adding up the left-ear high tone hearing ability and the right-ear low tone hearing ability; and a high-tone-assignment ear determining unit configured to decide to assign, in the dichotic hearing assistance, an audio signal in a range higher than the crossover frequency to a right ear and an audio signal in a range lower than the crossover frequency to a left ear, when the right-high-tone hearing ability is better than the left-high-tone hearing ability, and to decide to assign, in the dichotic hearing assistance, an audio signal in the range higher than the crossover frequency to the left ear and an audio signal in the range lower than the crossover frequency to the right ear, when the right-high-tone hearing ability is worse than the left-high-tone hearing ability.

With this structure, the hearing assistance suitability determining device according to the aspect of the present invention makes it possible to determine, in the dichotic hearing assistance, which of the left and right ears of the subject the high tone is assigned to, based only on the hearing ability information of the subject.

Furthermore, the hearing assistance suitability determining device may further include: an average hearing ability calculating unit configured to calculate an average hearing ability which is an average value of the hearing ability for the frequencies indicated by the hearing ability information; and a suitability correcting unit configured to decrease the suitability decided by the suitability deciding unit, when the average hearing ability is out of a predetermined range.

With this structure, the hearing assistance suitability determining device according to the aspect of the present invention makes it possible to properly determine whether or not the dichotic hearing assistance is suitable for a user whose hearing deterioration is little and a user whose hearing deterioration is significant.

Moreover, the hearing assistance suitability determining device may further include: a profile obtaining unit configured to obtain information indicating an age of the subject; and a suitability correcting unit configured to decrease the suitability decided by the suitability deciding unit, when the age of the subject is higher than a predetermined threshold.

With this structure, the hearing assistance suitability determining device according to the aspect of the present invention makes it possible to determine whether or not the dichotic hearing assistance is suitable, according to the age of the user.

Furthermore, the hearing assistance suitability determining device may further include a profile obtaining unit configured to obtain information indicating a period of use which is a period in which the subject has used a hearing aid; and a suitability correcting unit configured to decrease the suitability decided by the suitability deciding unit, when the period of use is less than a predetermined threshold.

With this structure, the hearing assistance suitability determining device according to the aspect of the present invention makes it possible to determine whether or not the dichotic hearing assistance is suitable, according to the period of hearing-aid use by the user.

Moreover, the hearing ability information obtaining unit may be configured to obtain, as the hearing ability information, right-ear hearing ability information which indicates a right-ear hearing ability of the subject for frequencies and left-ear hearing ability information which indicates a left-ear hearing ability of the subject for frequencies, and the hearing assistance suitability determining device may further include: a binaural difference calculating unit configured to calculate a binaural difference which is a difference between the right-ear hearing ability indicated by the right-ear hearing ability information and the left-ear hearing ability indicated by the left-ear hearing ability information; and a suitability correcting unit configured to decrease the suitability decided by the suitability deciding unit, when the binaural difference is greater than a predetermined threshold.

With this structure, the hearing assistance suitability determining device according to the aspect of the present invention makes it possible to properly determine whether or not the dichotic hearing assistance is suitable for the user whose auditory characteristics of the left and right ears are different from each other.

It is to be noted that the present invention can be realized not only as such a hearing assistance suitability determining device, but also as a hearing assistance suitability determining method having, as steps, characteristic units included in the hearing assistance suitability determining device, and as a program causing a computer to execute such characteristic steps. Needless to say, such a program can be distributed via recording media such as a CD-ROM and transmission media such as the Internet.

Further, the present invention can be realized as a semiconductor integrated circuit (LSI) which performs part or all of the functions of such a hearing assistance suitability determining device, as a hearing assistance adjustment device including such a hearing assistance suitability determining device, and as a hearing assistance adjustment system including such a hearing assistance adjustment device.

Advantageous Effects of Invention

Therefore, the present invention successfully provides the hearing assistance suitability determining device which makes it possible to readily determine the suitability of the subject for the dichotic hearing assistance.

BRIEF DESCRIPTION OF DRAWINGS

FIG. 1 is a diagram showing an example of an audiogram.
FIG. 2 is a block diagram showing a conventional hearing assistance adjustment device.
[FIG. 3]
FIG. 3 is a diagram showing examples of a hearing level.
FIG. 4 is a block diagram showing a conventional dichotic hearing assistance determining device.
FIG. 5 is a block diagram showing a hearing assistance adjustment system according to Embodiment 1 of the present invention.
FIG. 6 is a flowchart of hearing assistance adjustment processing according to Embodiment 1 of the present invention.
FIG. 7A is a diagram showing examples of a hearing level according to Embodiment 1 of the present invention.
FIG. 7B is a diagram showing examples of a determination algorithm for a hearing ability type according to Embodiment 1 of the present invention.
FIG. 8 is a flowchart of hearing ability type determination processing according to Embodiment 1 of the present invention.
FIG. 9A is a diagram showing an example of an audiogram for high-frequency plunging type according to Embodiment 1 of the present invention.
FIG. 9B is a diagram showing an example of an audiogram for chevron type according to Embodiment 1 of the present invention.
FIG. 9C is a diagram showing an example of an audiogram for flat type according to Embodiment 1 of the present invention.
FIG. 10A is a diagram showing relationships between hearing ability types and dichotic hearing assistance according to Embodiment 1 of the present invention.
FIG. 10B is a diagram showing an example of a suitability database according to Embodiment 1 of the present invention.
FIG. 11 is a diagram showing a screen display example displayed by a suitability display unit according to Embodiment 1 of the present invention.
FIG. 12 is a block diagram showing a modification of a hearing assistance adjustment device according to Embodiment 1 of the present invention.

FIG. 13 is a block diagram showing a hearing assistance adjustment device according to Embodiment 2 of the present invention.
FIG. 14 is a flowchart of hearing assistance adjustment processing according to Embodiment 2 of the present invention.
FIG. 15 is a diagram showing relationships between hearing levels and an application range of dichotic hearing assistance according to Embodiment 2 of the present invention.
FIG. 16 is a flowchart of a modification of hearing assistance adjustment processing according to Embodiment 2 of the present invention.
FIG. 17 is a block diagram showing a hearing assistance adjustment device according to Embodiment 3 of the present invention.
FIG. 18 is a flowchart of suitability correction processing according to Embodiment 3 of the present invention.
FIG. 19 is a flowchart of another example of suitability correction processing according to Embodiment 3 of the present invention.
FIG. 20 is a block diagram showing a hearing assistance adjustment device according to Embodiment 4 of the present invention.
FIG. 21 is a flowchart of suitability correction processing according to Embodiment 4 of the present invention.
FIG. 22 is a block diagram showing a hearing assistance adjustment device according to Embodiment 5 of the present invention.
FIG. 23 is a diagram showing an example of an audiogram according to Embodiment 5 of the present invention.
FIG. 24 is a flowchart of high-tone-assignment ear determination processing according to Embodiment 5 of the present invention.
FIG. 25 is a block diagram showing a hearing assistance adjustment device according to Embodiment 6 of the present invention.
FIG. 26 is a flowchart of high-tone-assignment ear determination processing according to Embodiment 6 of the present invention.
[FIG. 27]
FIG. 27 is a diagram showing a clinical evaluation test result according to Embodiment 6 of the present invention.

DESCRIPTION OF EMBODIMENTS

The following describes in detail embodiments of a hearing assistance suitability determining device according to the present invention with reference to the drawings.

(Embodiment 1)

A hearing assistance suitability determining device 120 according to Embodiment 1 of the present invention determines a suitability of a subject for dichotic hearing assistance, based on a hearing ability type defined by a tendency in a change in a hearing ability of the subject for frequencies.

Therefore, the hearing assistance suitability determining device 120 according to Embodiment 1 of the present invention makes it possible to readily determine the suitability of the subject for the dichotic hearing assistance.

Figure 1:
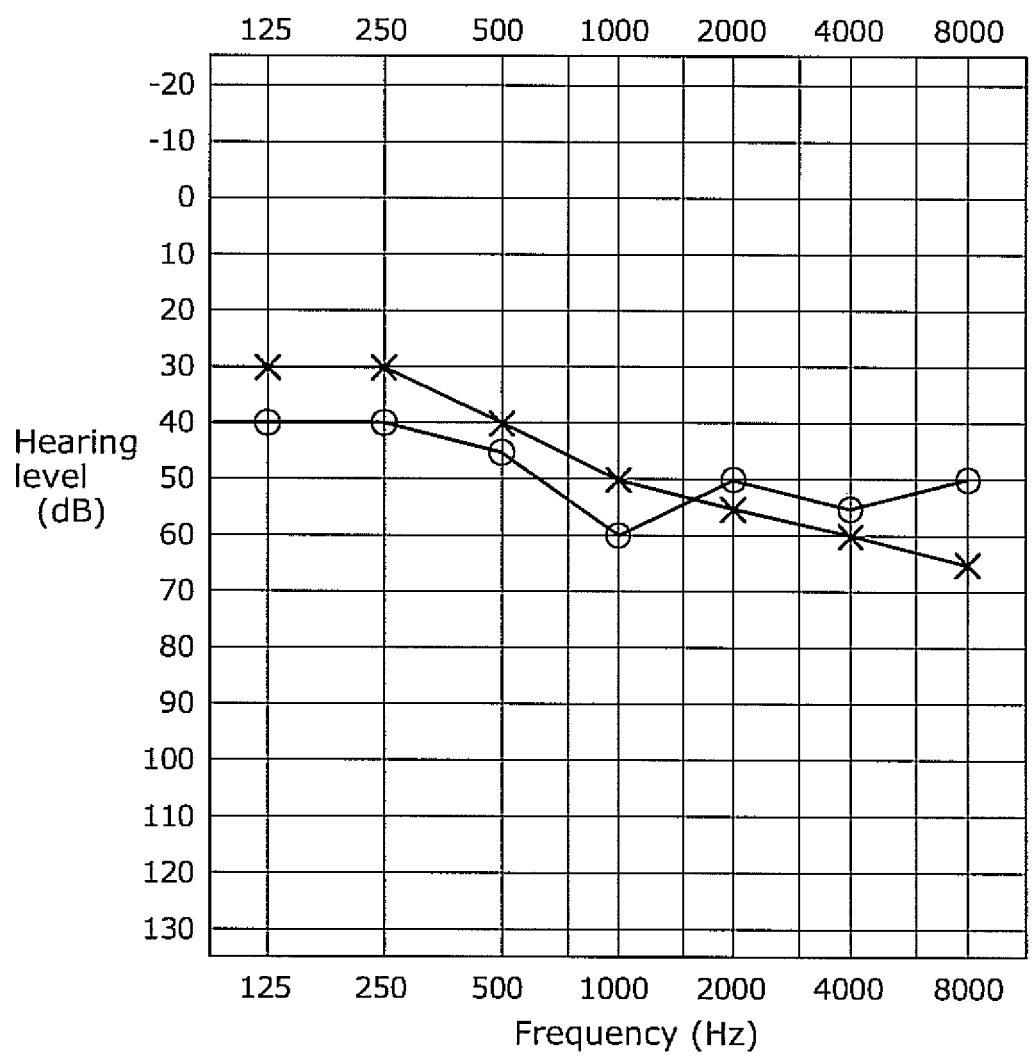
[FIG. 1]
Figure 2:
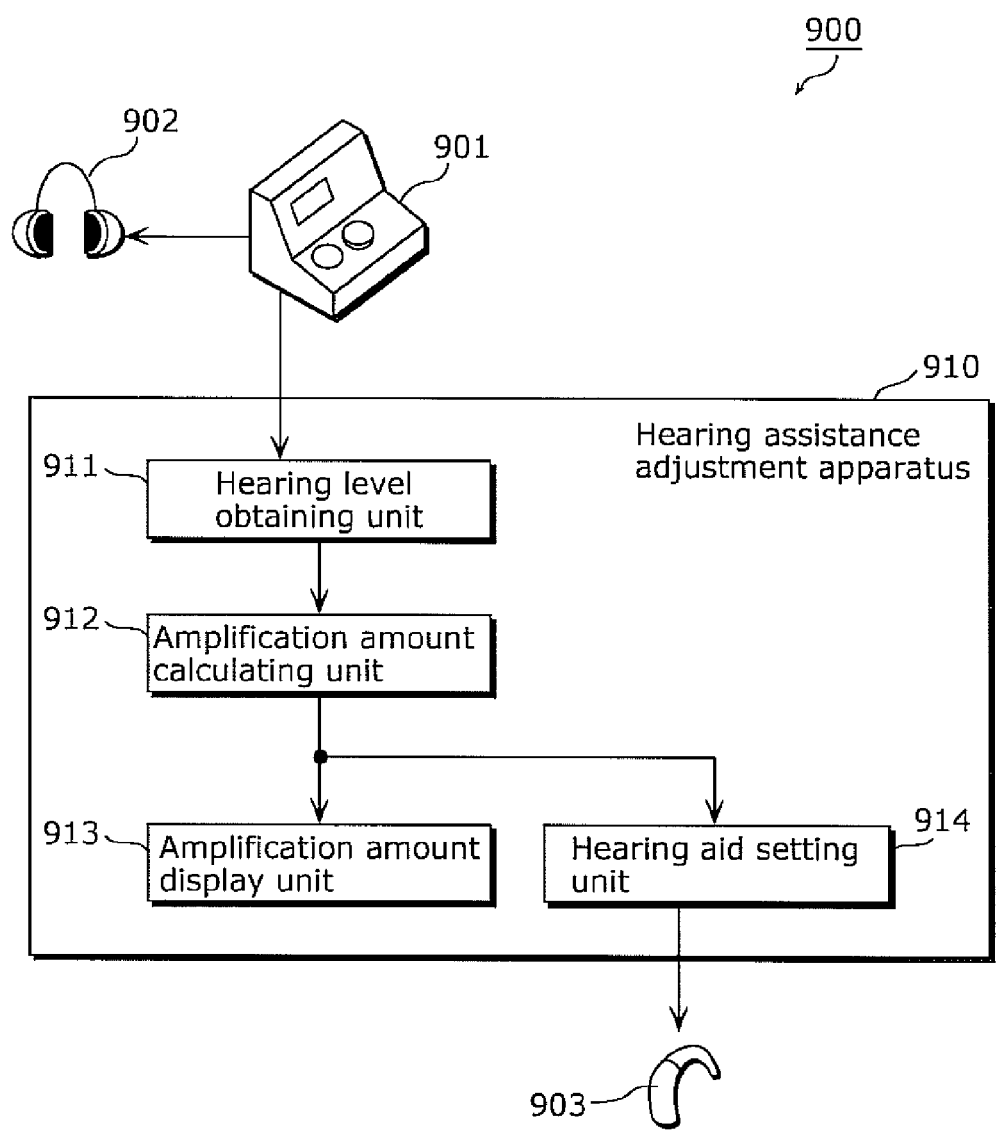
[FIG. 2]
Figure 4:
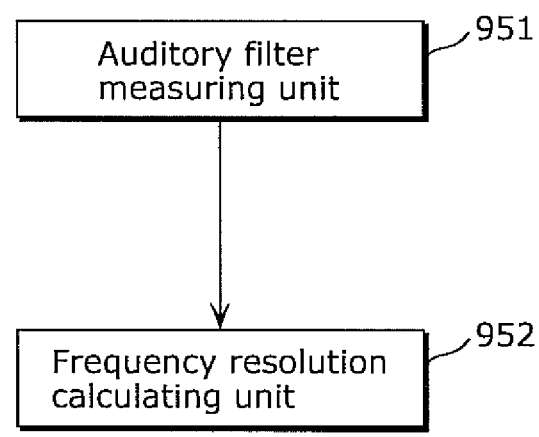
[FIG. 4]
Figure 5:
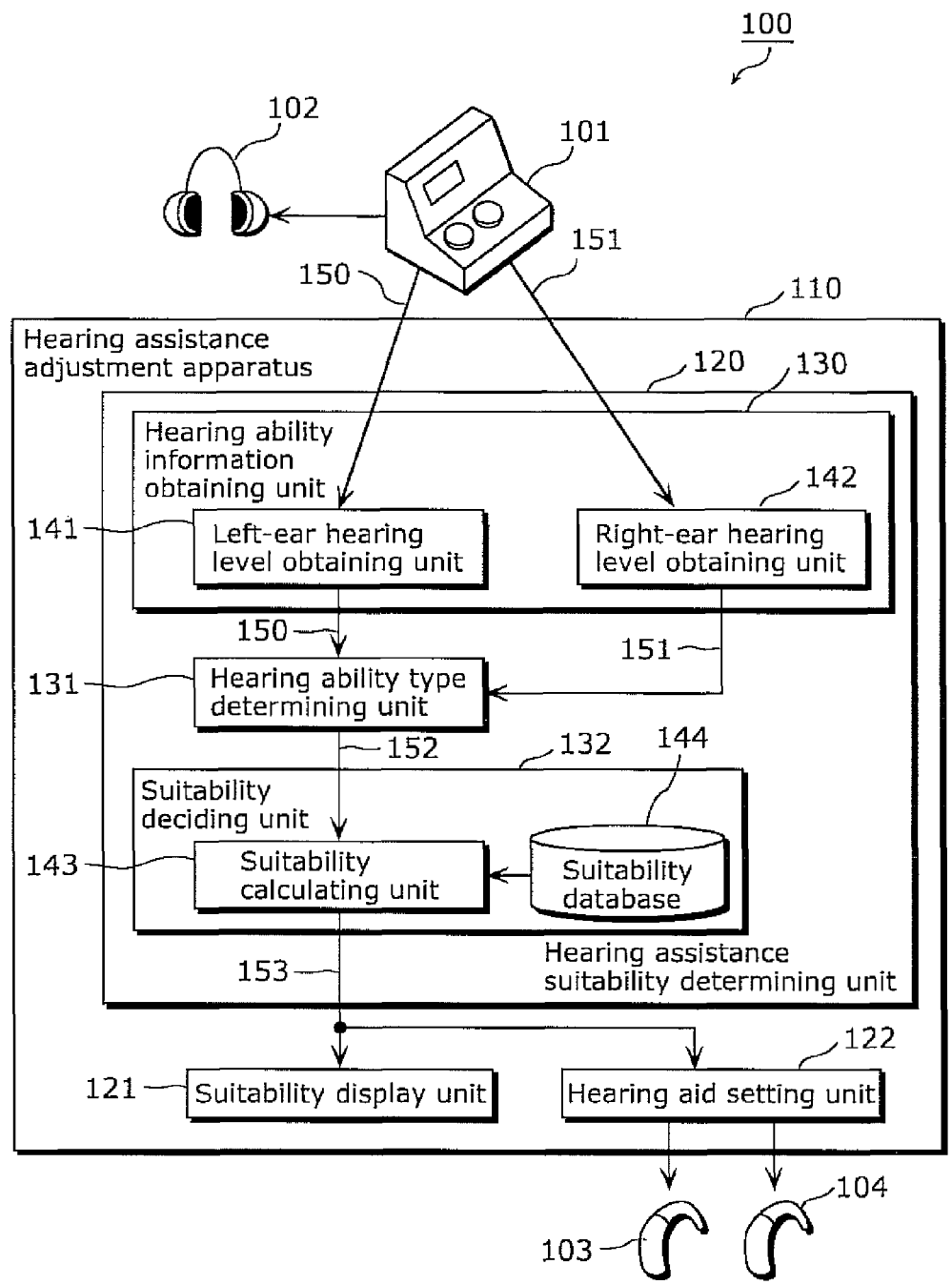
[FIG. 5]

FIG. 5 is a block diagram showing a hearing assistance adjustment system 100 according to Embodiment 1 of the present invention.

The hearing assistance adjustment system 100 shown in FIG. 5 includes an audiometer 101, headphones 102, a left-ear hearing aid 103, a right-ear hearing aid 104, and a hearing assistance adjustment device 110.

The audiometer 101 produces pure tones, and causes a subject (a user of the hearing aids) to hear the produced pure tones via the headphones 102. Moreover, whether or not the subject has heard the tones is notified to a measuring person or the audiometer 101 through an interface. In this way, the audiometer 101 measures hearing levels of the subject. More specifically, the audiometer 101 measures a hearing level of the subject for each frequency, and provides hearing ability information indicating the measurement result. The hearing ability information includes: left-ear hearing ability information 150 which indicates a hearing ability of a left ear of the subject for the frequencies; and right-ear hearing ability information 151 which indicates a hearing ability of a right ear of the subject for the frequencies.

Here, the hearing level is the minimum sound pressure level at which the subject can hear. In other words, a low hearing level means a better hearing ability (better hearing), and a high hearing level means a worse hearing ability (sever hearing impairment).

The hearing assistance adjustment device 110 adjusts hearing assistance processing for the left-ear hearing aid 103 and the right-ear hearing aid 104, based on the measurement result of the hearing levels by the audiometer 101. The hearing assistance adjustment device 110 includes a hearing assistance suitability determining device 120, a suitability display unit 121, and a hearing aid setting unit 122.

The hearing assistance suitability determining device 120 determines a suitability of the subject for dichotic hearing assistance, using the hearing ability information of the subject. Here, the dichotic hearing assistance is a hearing assistance method in which an input signal is divided on the frequency axis to be assigned to respective left and right ears.

The hearing assistance suitability determining device 120 includes a hearing ability information obtaining unit 130, a hearing ability type determining unit 131, and a suitability deciding unit 132.

The hearing ability information obtaining unit 130 obtains the hearing ability information measured by the audiometer 101. The hearing ability information obtaining unit 130 includes: a left-ear hearing level obtaining unit 141 which obtains left-ear hearing ability information 150; and a right-ear hearing level obtaining unit 142 which obtains right-ear hearing ability information 151.

The hearing ability type determining unit 131 determines, among hearing ability types each of which is defined by a tendency in a change in a hearing ability with respect to frequencies, a hearing ability type 152 of a hearing ability indicated by the hearing ability information.

The suitability deciding unit 132 decides a suitability 153 of the subject for the dichotic hearing assistance, based on the hearing ability type 152 determined by the hearing ability type determining unit 131. The suitability deciding unit 132 includes a suitability calculating unit 143 and a suitability database 144.

The suitability database 144 is a table which shows a correspondence relationship between each of the hearing ability types and one of suitabilities of the subject for the dichotic hearing assistance.

The suitability calculating unit 143 decides, with reference to the suitability database 144, a suitability 153 of the subject for the dichotic hearing assistance, based on a suitability corresponding, in the suitability database 144, to the hearing ability type determined by the hearing ability type determining unit 131.

The suitability display unit 121 displays the suitability 153 to notify an operator.

The hearing aid setting unit 122 adjusts hearing assistance processing for the left-ear hearing aid 103 and the right-ear hearing aid 104, based on the suitability 153 determined by the hearing assistance suitability determining device 120.

Next, an operation of the hearing assistance adjustment device 110 is described.

Figure 6:
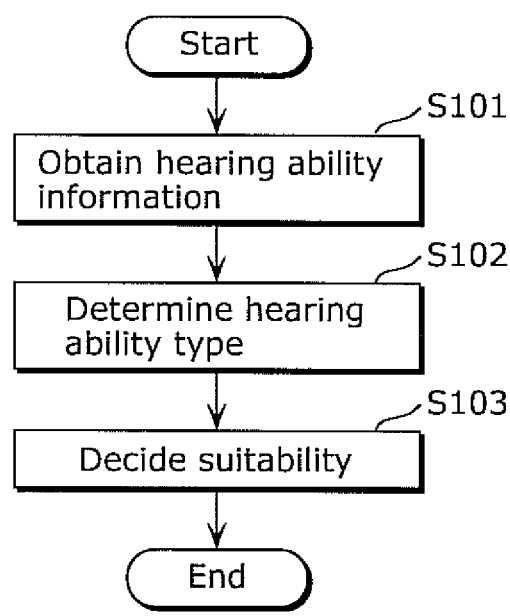
[FIG. 6]

FIG. 6 is a flowchart of a hearing assistance processing adjustment method performed by the hearing assistance adjustment device 110.

First, the hearing ability information obtaining unit 130 obtains the left-ear hearing ability information 150 and the right-ear hearing ability information 151 (S101).

Then, the hearing ability type determining unit 131 classifies a hearing ability of a hearing-aid user into a hearing ability type, based on a general shape of frequency characteristics of left- and right-hearing levels indicated by the left-ear hearing ability information 150 and the right-ear hearing ability information 151 (S101). The classification is performed in the following manner, for instance.

Figure 7:
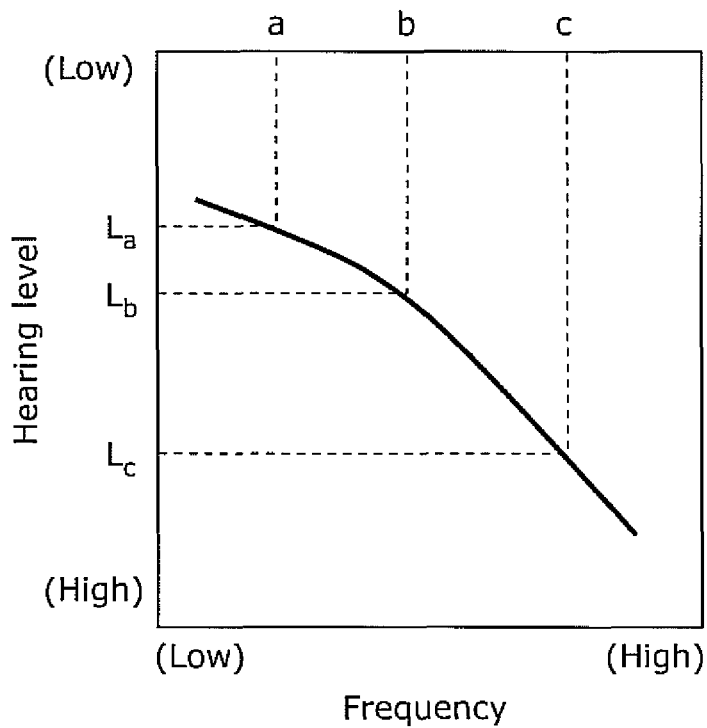
[FIG. 7A]
[FIG. 7B]

FIG. 7A is a diagram showing examples of a hearing level when average values of left- and right-hearing levels at three frequencies a, b, and c (a<b<c) are La, Lb, and Lc. The horizontal axis of FIG. 7A indicates a frequency, and that the frequency becomes higher to the right. The vertical axis of FIG. 7A indicates a hearing level, and that the hearing level becomes higher to the bottom, that is, a deterioration in hearing is larger to the bottom.

FIG. 7B is a diagram showing examples of a determination algorithm for a hearing ability type.

When La<Lb<Lc, that is, a hearing ability decreases as a frequency becomes higher, the hearing ability type determining unit 131 classifies the hearing ability into a high-frequency sloping type.

However, when La≤Lb<<Lc, that is, a hearing level difference in a range having a relatively high frequency (frequency c) is above a certain level, instead of a hearing level difference in a rage having a relatively low frequency (frequencies a and b), the hearing ability type determining unit 131 classifies a hearing ability into a high-frequency plunging type.

Furthermore, when La>Lb<Lc, that is, a hearing ability increases once and then decreases as a frequency becomes higher, the hearing ability type determining unit 131 classifies the hearing ability into a chevron type.

Moreover, when La≈Lb≈Lc, the hearing ability type determining unit 131 classifies a hearing ability into a flat type.

Here, although an average value of the left- and right-hearing levels is used for the classification so as to comprehensively determine the left- and right-hearing levels, the hearing levels of one of the ears which has a less deterioration in hearing than the other ear may be used.

Furthermore, it is possible to perform the determination using the following algorithm as a specific example.

Figure 8:
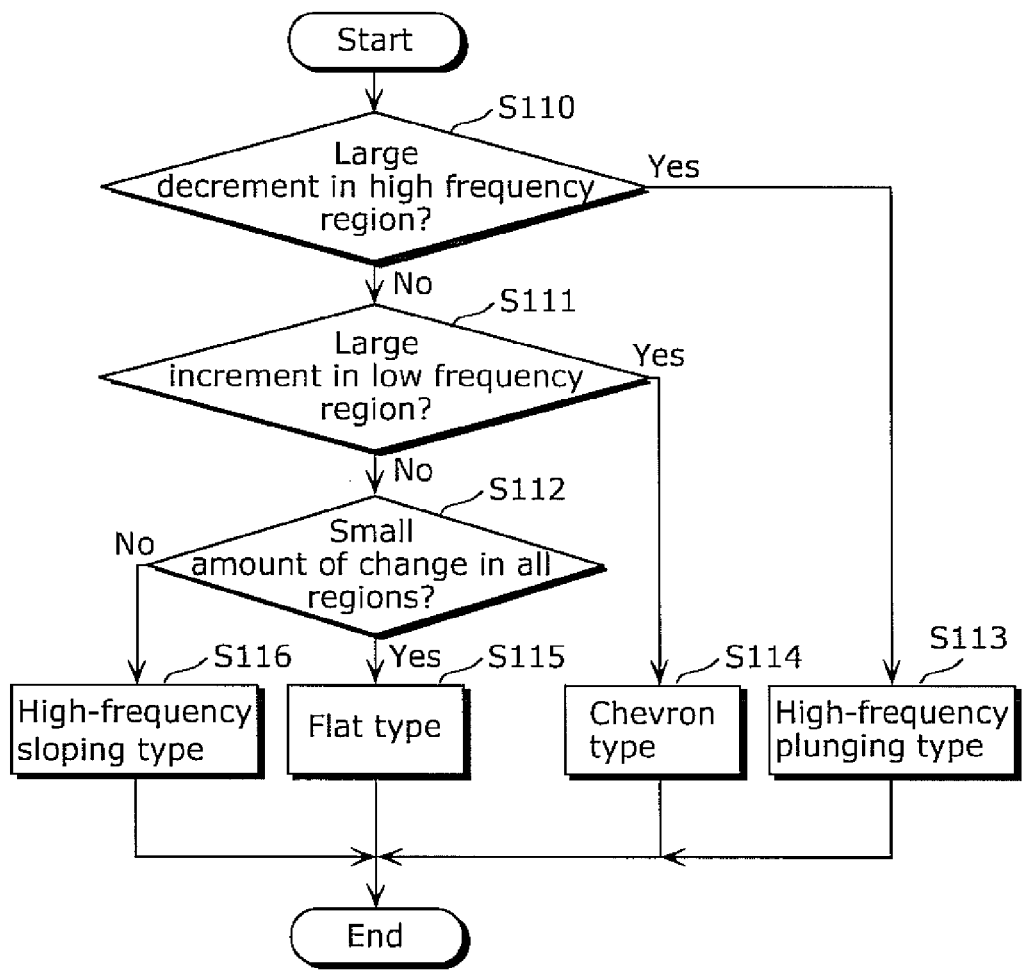
[FIG. 8]

FIG. 8 is a flowchart showing an example of a hearing ability type classification algorithm.

First, the hearing ability type determining unit 131 determines whether or not a decrement of a hearing ability in a frequency range higher than a predetermined frequency is greater than a first threshold (S110). When the decrement of the hearing ability in the frequency region higher than the predetermined frequency is greater than the first threshold (Yes in S110), the hearing ability type determining unit 131 classifies a hearing ability into the high-frequency plunging type (S113).

Figure 9A:
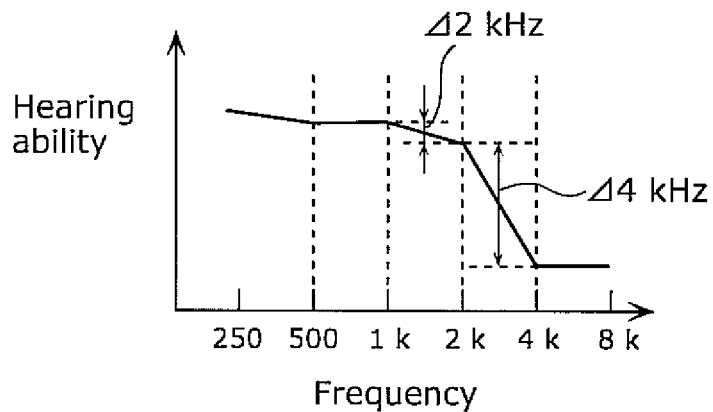
[FIG. 9A]

For example, as shown in FIG. 9A, the hearing ability type determining unit 131 calculates decrements $\Delta 1$ kHz, $\Delta 2$ kHz, and $\Delta 4$ kHz by subtracting a hearing level at an octave lower from each of hearing levels at 1 kHz, 2 kHz, and 4 kHz. In the case where one or more of the calculated decrements $\Delta 1$ kHz, $\Delta 2$ kHz, and $\Delta 4$ kHz are greater than a predetermined value (preferably above 20 dB, e.g., 30 dB), the hearing ability type determining unit 131 determines a hearing ability type of a hearing ability as the high-frequency plunging type.

It is to be noted that although, here, the hearing ability type determining unit 131 calculates the decrements $\Delta 1$ kHz, $\Delta 2$ kHz, and $\Delta 4$ kHz, the hearing ability type determining unit 131 may calculate at least one of the decrements $\Delta 1$ kHz, $\Delta 2$ kHz, and $\Delta 4$ kHz. In addition, it is preferred that the hearing ability type determining unit 131 calculates at least the decrements $\Delta 2$ kHz and $\Delta 4$ kHz.

Moreover, the hearing ability type determining unit 131 may calculate a decrement of a hearing level other than the hearing levels at 1 kHz, 2 kHz, and 4 kHz. For instance, the hearing ability type determining unit 131 may calculate decrements $\Delta 500$ Hz, $\Delta 1$ kHz, $\Delta 2$ kHz, and $\Delta 4$ kHz.

Furthermore, the hearing ability type determining unit 131 determines whether or not an increment of a hearing ability in a frequency range lower than a predetermined frequency is greater than a predetermined threshold (S111). When the increment of the hearing ability in the frequency range lower than the predetermined frequency is greater than the predetermined threshold (Yes in S111), the hearing ability type determining unit 131 classifies the hearing ability into the chevron type (S114).

Figure 9B:
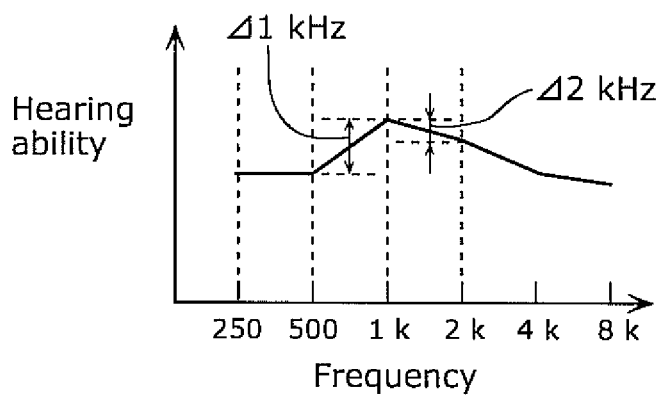
[FIG. 9B]

For example, as shown in FIG. 9B, the hearing ability type determining unit 131 calculates increments $\Delta 500$ Hz, $\Delta 1$ kHz, and $\Delta 2$ kHz by subtracting a hearing level at an octave lower from each of hearing levels at 500 Hz, 1 kHz, and 2 kHz. In the case where one or more of the calculated increments $\Delta 500$ Hz, $\Delta 1$ kHz, and $\Delta 2$ kHz are greater than a predetermined value (preferably above 10 dB, e.g., 10 dB), the hearing ability type determining unit 131 determines a hearing ability type of the hearing ability as the chevron type.

It is to be noted that although, here, the hearing ability type determining unit 131 calculates the increments $\Delta 500$ Hz, $\Delta 1$ kHz, and $\Delta 2$ kHz, the hearing ability type determining unit 131 may calculate at least one of the increments $\Delta 500$ Hz, $\Delta 1$ kHz, and $\Delta 2$ kHz. In addition, it is preferred that the hearing ability type determining unit 131 calculates at least the increments $\Delta 500$ Hz and $\Delta 1$ kHz.

Moreover, the hearing ability type determining unit 131 may calculate an increment of a hearing level other than the hearing levels at 500 Hz, 1 kHz, and 2 kHz.

Furthermore, the hearing ability type determining unit 131 determines whether or not an amount of change in a hearing ability in all frequencies indicated by hearing ability information is smaller than a predetermined second threshold (S112). When the amount of change in the hearing ability in all the frequencies indicated by the hearing ability information is smaller than the predetermined second threshold (Yes in S112), the hearing ability type determining unit 131 classifies the hearing ability into the flat type (S115).

Figure 9C:
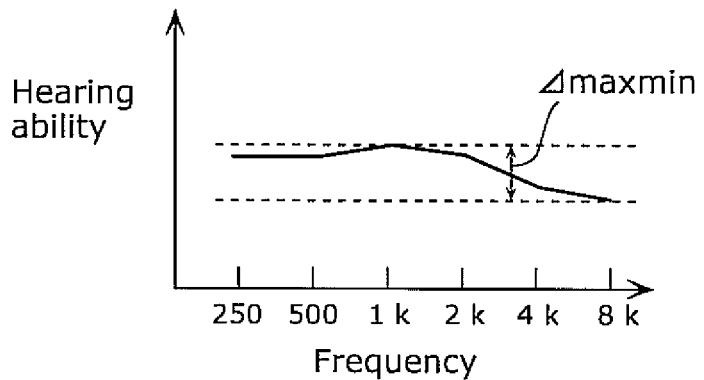
[FIG. 9C]

For instance, as shown in FIG. 9C, in the case where a difference between the maximum and minimum values $\Delta$maxmin of the hearing levels in all the frequency ranges is less than a predetermined value (preferably above 20 dB, e.g., 30 dB), the hearing ability type determining unit 131 determines a hearing ability type of the hearing ability as the flat type.

Moreover, when the hearing ability type of the hearing ability does not correspond to any of the high-frequency plunging type, chevron type, and flat type (No in S110, No in S111, and No in S112), the hearing ability type determining unit 131 determines the hearing ability type of the hearing ability as the high-frequency sloping type (S116).

In this way, the hearing ability type determining unit 131 classifies the hearing ability into one of the hearing ability types based on a general shape of frequency characteristics of the hearing levels, and provides the suitability calculating unit 143 with information about the classified hearing ability type 152.

It is to be noted that a sequence of the steps S110 to S112 shown in FIG. 8 is an example, and an execution sequence of the steps S110 to S112 may be changed.

In addition, the hearing ability type determining unit 131 may further determine a hearing ability type other than the high-frequency sloping type, high-frequency plunging type, chevron type, and flat type. Examples of hearing ability types determined by the hearing ability type determining unit 131 may include a hearing ability type (low-frequency impairing type) in which a hearing ability increases as a frequency becomes higher and a hearing ability type (v-shaped type) in which the hearing ability decreases once and then increases as the frequency becomes higher.

The suitability calculating unit 143 calculates, with reference to the suitability database 144, the suitability 153 for the dichotic hearing assistance corresponding to the hearing ability type 152 classified by the hearing ability type determining unit 131.

The suitability database 144 accumulates, as an index indicating a suitability of a subject for dichotic hearing assistance, statistical values such as a probability for effectiveness a of the dichotic hearing assistance in clarity improvement and an amount of improvement expected (amount of expected improvement $\beta$) due to the dichotic hearing assistance, in association with one of the hearing ability types.

Here, the clarity is a probability that a subject can hear a test speech sound in a clinical test. For example, the test speech sound is a sound produced when each of a man and a woman who have speech training experience utters a total of 40 types of syllables composed of five types of preceding vowels (the Japanese vowels: a, i, u, e, and o) and eight types of subsequent sounds (Japanese words: pa, ta, ka, ba, da, ga, sa, and za). Furthermore, the test speech sound is given to the ears of the subject, and the subject is instructed to write down exactly what the subject heard on an answer sheet. A probability (accuracy rate) that the answered speech sound and the actual test speech sound match each other is the clarity.

Moreover, as stated above, the deterioration in frequency resolution is the problem caused by the principle different from the reduced hearing sensitivity. It was unknown as to whether or not there is a relationship between them, and, if there is, what kind of relationship it is. However, performing dichotic hearing assistance on hearing-impaired people classified into various hearing ability types has found out effectiveness of the hearing ability types and the dichotic hearing assistance, and a degree of clarity improvement.

Figures 10A, 10B:
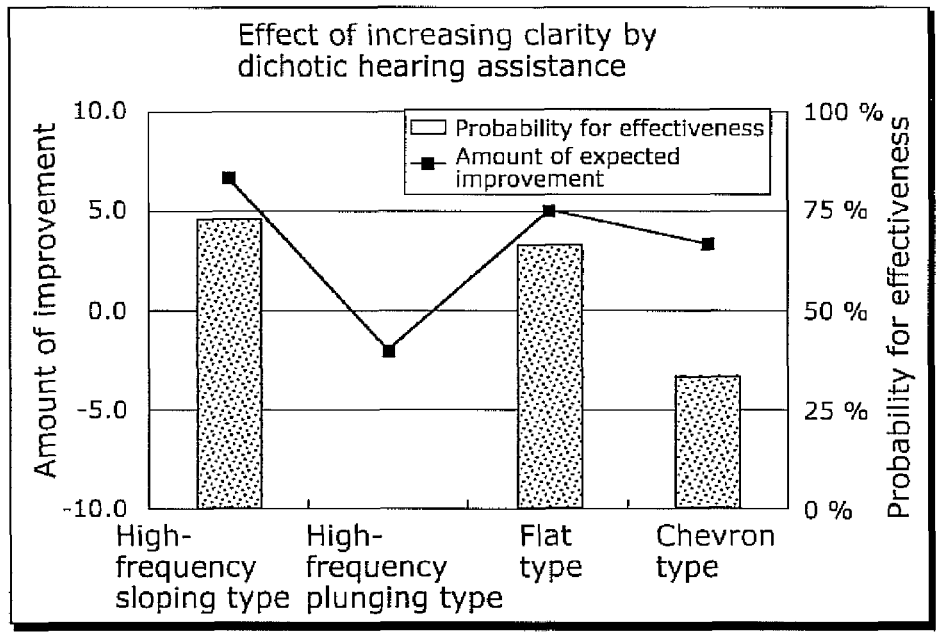
[FIG. 10A]
[FIG. 10B]

Each of FIG. 10A and FIG. 10B shows a rate (probability for effectiveness a) of hearing-impaired people whose sound clarity has been improved by performing dichotic hearing assistance on the hearing-impaired people each having one of the hearing ability types, and an average value (amount of expected improvement β) of the sound clarity improved or deteriorated by doing the same.

The horizontal axis of a graph shown in FIG. 10A indicates the hearing ability types, a scale on the right-side vertical axis indicates the probability for effectiveness a for a bar graph, and a scale on the left-side vertical axis indicates the amount of expected improvement β for a line graph.

The probability for effectiveness a is an index indicating how many hearing-impaired people can feel the clarity improvement due to the dichotic hearing assistance. More specifically, the probability for effectiveness α is a probability which is obtained in advance through experiment and with which the clarity is improved, by using the dichotic hearing assistance, by more than a predetermined threshold (e.g., 5%).

The amount of expected improvement β is an index indicating how much the clarity is improved when the dichotic hearing assistance is effective. More specifically, the amount of expected improvement β is an average value of amounts of clarity improvement, which are obtained in advance through experiment, of a subject for which the dichotic hearing assistance is effective.

As shown in FIG. 10B, the probability for effectiveness α and the amount of expected improvement β are accumulated in the suitability database 144 as information that can be referred to, for each hearing ability type, in a table.

The suitability 153 is lowest in the high-frequency plunging type, and increases in an order of the chevron type, flat type, and high-frequency sloping type. To put it differently, the suitability deciding unit 132 decides that the suitability 153 is to be highest when the hearing ability type is the high-frequency sloping type, and decides that the suitability 153 is to decrease in an order of the flat type, chevron type, and high-frequency plunging type.

It is to be noted that the suitability database 144 may include, for each of crossover frequencies fc of the dichotic hearing assistance, a table, and the suitability calculating unit 143 may switch between the tables and refer to a switched table.

Here, the crossover frequency fc is a frequency which distinguishes a vowel and a consonant, and is a value between a first formant frequency having large energy among vowels and a second formant frequency characterizing consonants. It is to be noted that although a suitable crossover frequency fc differs depending on vocal characteristics of an utterer and aural characteristics of a user, the crossover frequency fc is generally a frequency in a range of 800 Hz to approximately 2000 Hz. In the case of performing the dichotic hearing assistance, a sound is divided by the crossover frequency fc, and one of the divided sound is assigned to one of the right and left ears, and the other one of the divided sound is assigned to the other one of the right and left ears.

Furthermore, the suitability database 144 may include tables which differ depending on a language to be used or a race of a patient, and the suitability calculating unit 143 may switch between the tables and refer to a switched table. Moreover, the suitability database 144 may include correction data for correcting, with respect to a basic database, values in a table by destination.

The suitability calculating unit 143 calculates a suitability ω (suitability 153) with reference to the information which is accumulated in the suitability database 144 and which includes the probability for effectiveness α of and the amount of expected improvement β by the dichotic hearing assistance, with the hearing ability type 152 classified by the hearing ability type determining unit being a key. The suitability ω may be a value calculated by using the probability for effectiveness α and the amount of expected improvement β as indicated below (Equation 1), a value calculated by using one of the probability for effectiveness α and the amount of expected improvement β, or the probability for effectiveness α or the amount of expected improvement β itself.

[Math. 1]

$$\omega = \left(\frac{\alpha \times \beta}{0.05}\right) \quad \text{(Equation 1)}$$

The suitability display unit 121 displays information on a screen of a computer or the like so as to notify a user oneself of the hearing assistance adjustment device 110 of a suitability. In addition, the suitability display unit 121 may notify the suitability simply using illumination of LED or the like, and may be a display unit which notifies the suitability in one way or another.

Figure 11:
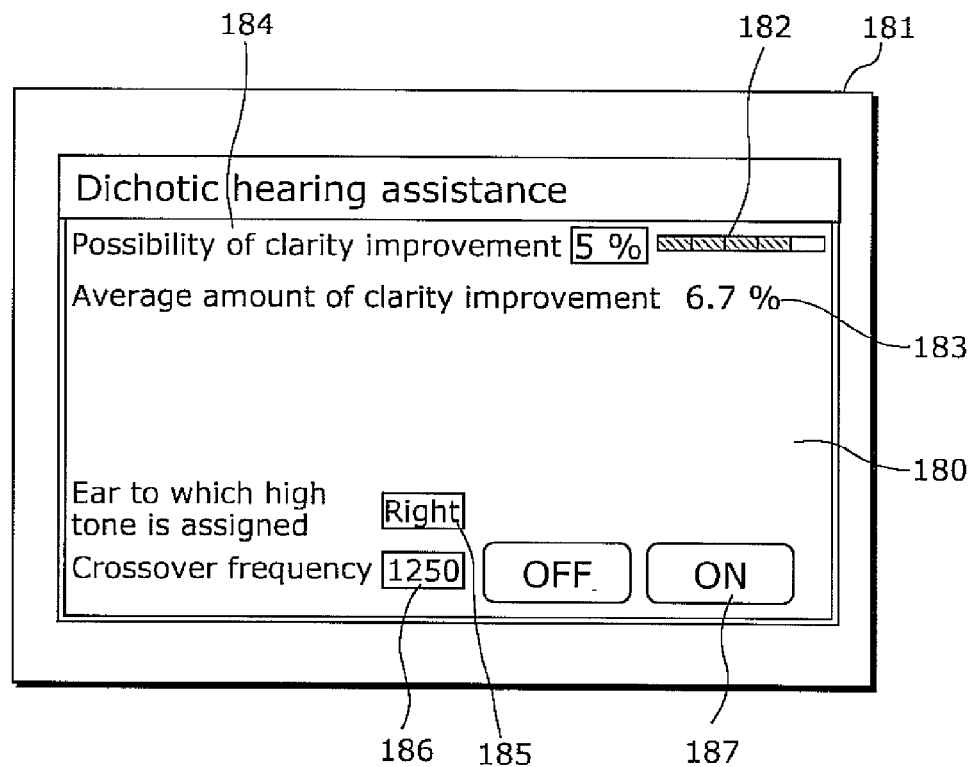
[FIG. 11]

FIG. 11 is a diagram showing an image of a screen display by the suitability display unit 121. For instance, the suitability display unit 121 displays the suitability 153 in a suitability display region 180 on a screen 181. It is to be noted that although the suitability display unit 121 displays, as a bar graph, the probability for effectiveness α in a probability for effectiveness display region 182 in FIG. 11, the probability for effectiveness α may be displayed as a value such as a percentage, as a text such as suitable and unsuitable, as a pie chart, as an icon, and so on, or may be represented by brightness of display colors.

In FIG. 11, a determination standard input field 184 shows 5%. A determination standard of the probability for effectiveness α is changed with reference to the determination standard input field 184. Moreover, the suitability calculating unit 143 reflects, in processing, a determination standard value inputted to the determination standard input field 184. Stated differently, the suitability calculating unit 143 calculates, as the probability for effectiveness α, a probability that the clarity is improved by more than the determination standard inputted to the determination standard input field 184.

Furthermore, the suitability display unit 121 may not only display the suitability but also may concurrently display the average amount of clarity improvement β in an average amount of improvement display region 183. It is to be noted that although the suitability display unit 121 displays, as a value, the average amount of clarity improvement β in FIG. 11, the average amount of clarity improvement β may be displayed with a graph or an icon.

Moreover, a high-tone-assigned ear input field 185 for inputting whether a high tone is assigned to the left or right ear may be provided so that a case where hearing ability types of the left and right ears differ from each other can be addressed. In the case where, as described later, it is predictable as to whether the high tone should be assigned to the left or right ear, based on hearing ability information, the suitability display unit 121 may display a prediction result as an initial value of the high-tone-assigned ear input field 185.

Furthermore, a crossover frequency input field 186 for inputting a crossover frequency may be provided. In this instance, in the case where a crossover frequency which provides the largest amount of improvement is predictable based on hearing ability information, the suitability display unit 121 may display a prediction result as an initial value of the crossover frequency input field 186.

Further, an interface such as a button 187 may be provided so that the user of the hearing assistance adjustment device 110 can decide whether or not dichotic hearing assistance is to be performed eventually. Here, the suitability display region 180 itself does not need to be the interface, and display colors of the suitability display region 180 may be changed through operation of the interface.

In the case where the suitability 153 is greater than a predetermined standard (e.g., greater than 70% or the like) or the case where the performance of dichotic hearing assistance is decided through the interface or the like, the hearing aid setting unit 122 sets the left-ear hearing aid 103 and the right-ear hearing aid 104 so that dichotic hearing assistance processing is performed. For example, the hearing aid setting unit 122 sends, to the left-ear hearing aid 103 and the right-ear hearing aid 104, information indicating whether or not the dichotic hearing assistance processing is to be performed, and sets the left-ear hearing aid 103 and the right-ear hearing aid 104 so that a process of dividing an audio signal by a predetermined crossover frequency and outputting the divided audio signal is performed. Moreover, for instance, the hearing aid setting unit 122 may decide a crossover frequency based on hearing levels, and send, to the left-ear hearing aid 103 and the right-ear hearing aid 104, information about the decided crossover frequency.

As stated above, the hearing assistance adjustment device 110 according to Embodiment 1 of the present invention makes it possible to determine whether or not the dichotic hearing assistance is suitable for the subject and to set the dichotic hearing assistance, by only measuring the hearing levels.

The above has described the example where the hearing ability type determining unit 131 determines, among the hearing ability types, the hearing ability type corresponding to the hearing ability of the subject, the hearing ability type determining unit 131 may calculate a possibility that the hearing ability of the subject corresponds to each of the hearing ability types.

Figure 12:
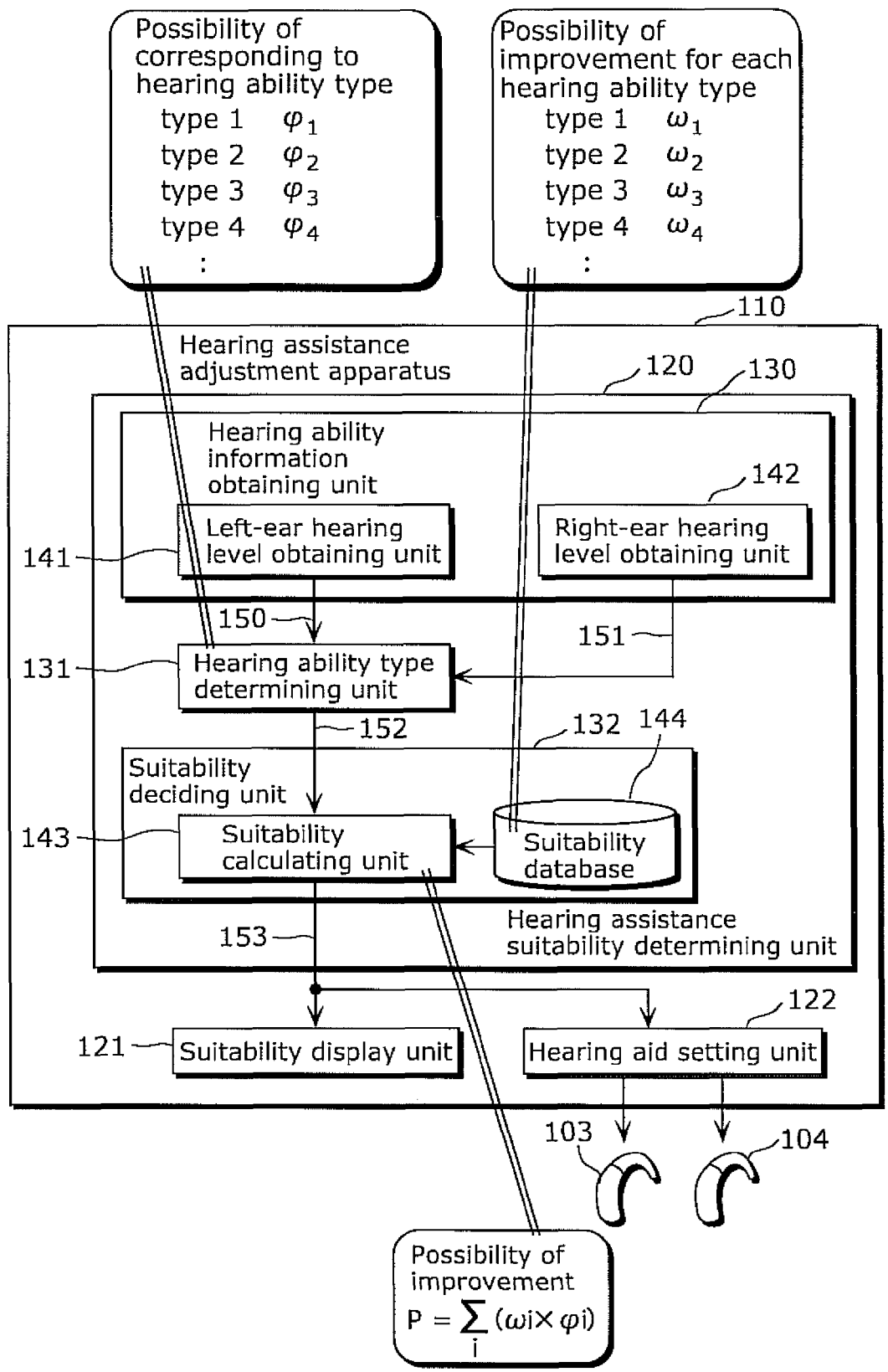
[FIG. 12]

FIG. 12 is a diagram showing a structure of the hearing assistance adjustment device 110 in this case. It is to be noted that type1, type2, type3, and so on shown in FIG. 12 indicate hearing ability types such as the above-mentioned high-frequency sloping type, high-frequency plunging type, chevron type, and flat type.

It is possible to calculate a possibility φ of corresponding to each of the hearing ability types, by using the following algorithm as a specific example.

As shown in FIG. 9A, the hearing ability type determining unit 131 calculates the decrements Δ1 kHz, Δ2 kHz, and Δ4 kHz by subtracting the hearing level at the octave lower from each of the hearing levels at 1 kHz, 2 kHz, and 4 kHz. Then, the hearing ability type determining unit 131 calculates a possibility φ2 of corresponding to the high-frequency plunging type, by using Equation 2 below.

[Math. 2]

$$\phi 2=(max(\Delta 1\text{ kHz}, \Delta 2\text{ kHz}, \Delta 4\text{ kHz})-10)/20 \quad \text{(Equation 2)}$$

The hearing ability type determining unit 131, however, assumes φ2=1 in the case where φ2 exceeds 1, and φ2=0 in the case where φ2 becomes negative.

Furthermore, as shown in FIG. 9B, the hearing ability type determining unit 131 calculates the increments Δ500 Hz, Δ1 kHz, and Δ2 kHz by subtracting the hearing level at the octave lower from each of the hearing levels at 500 Hz, 1 kHz, and 2 kHz. Then, the hearing ability type determining unit 131 calculates a possibility φ3 of corresponding to the chevron type, by using Equation 3 below.

[Math. 3]

$$\phi 3=min(\Delta 500\text{ Hz}, \Delta 1\text{ kHz}, \Delta 2\text{ kHz})/(-10) \quad \text{(Equation 3)}$$

The hearing ability type determining unit 131, however, assumes φ3=1 in the case where φ3 exceeds 1, and φ3=0 in the case where φ3 becomes negative.

Moreover, as shown in FIG. 9C, the hearing ability type determining unit 131 calculates the difference between the maximum and minimum values Δmaxmin of the hearing levels in the frequency ranges. Then, the hearing ability type determining unit 131 calculates a possibility φ4 of corresponding to the flat type, by using Equation 4 below.

[Math. 4]

$$\phi 4=1-(\Delta maxmin-30)/10 \quad \text{(Equation 4)}$$

The hearing ability type determining unit 131, however, assumes φ4=1 in the case where φ4 exceeds 1, and φ4=0 in the case where φ4 becomes negative.

Furthermore, the hearing ability type determining unit 131 calculates a possibility φ1 of corresponding to the high-frequency sloping type, by using Equation 5 below.

[Math. 5]

$$\phi 1=1-(\phi 2+\phi 3+\phi 4)/3 \quad \text{(Equation 5)}$$

The hearing ability type determining unit 131, however, assumes φ1=0 in the case where φ1 becomes negative.

Next, as shown below (Equation 6), the suitability calculating unit 143 calculates, for each of the hearing ability types, a multiplication value (ω×φ) by multiplying each of the possibilities 1 to 4 corresponding to one of the hearing ability types by a suitability ω of each hearing ability type which is calculated from the suitability database 144, and calculates the suitability 153 (P) by adding up the multiplication value calculated for each hearing ability type.

[Math. 6]

$$P = \sum_i (\omega_i \times \phi_i) \quad \text{(Equation 6)}$$

With such a structure, it is possible to properly evaluate whether or not the dichotic hearing assistance is applied even in the case where it is difficult to classify the hearing ability of the subject into a specific hearing ability type.

Moreover, as another implementation according to Embodiment 1 of the present invention, when a hearing ability type of a hearing-aid user is already known such as when the hearing-aid user replaces an old hearing aid with a new one, the hearing ability type may be directly inputted to the suitability calculating unit 143 without passing through the hearing ability information obtaining unit 130 and the hearing ability type determining unit 131.

Alternatively, the audiometer 101 and the hearing assistance adjustment device 110 or the hearing assistance suitability determining device 120 may be combined.

Furthermore, when frequency characteristics of left- and right-hearing levels are similar to each other, the hearing ability information obtaining unit 130 may obtain only the hearing levels of one of the left and right ears.

As described above, the hearing assistance adjustment device 110 according to Embodiment 1 of the present invention makes it possible to determine whether or not the dichotic hearing assistance is suitable for the user whose auditory characteristics are difficult to be classified into one of the hearing ability types, and to set the dichotic hearing assistance, only by measuring the hearing levels of the user.

Moreover, although the above embodiment has described, as the example, the hearing assistance adjustment system 100, the hearing assistance adjustment device 110, and the hearing assistance processing adjustment method which make it possible to adjust the hearing assistance processing of the hearing aid, the present invention is not limited to this, and enables similar determination and setting in other audio equipment.

Furthermore, the hearing assistance adjustment device 110 may include only one of the suitability display unit 121 and the hearing aid setting unit 122.

(Embodiment 2)

Embodiment 2 of the present invention describes a modification of the hearing assistance adjustment device 110 according to Embodiment 1. A hearing assistance adjustment device 210 according to Embodiment 2 of the present invention corrects a suitability according to an average hearing level of a subject.

Figure 13:
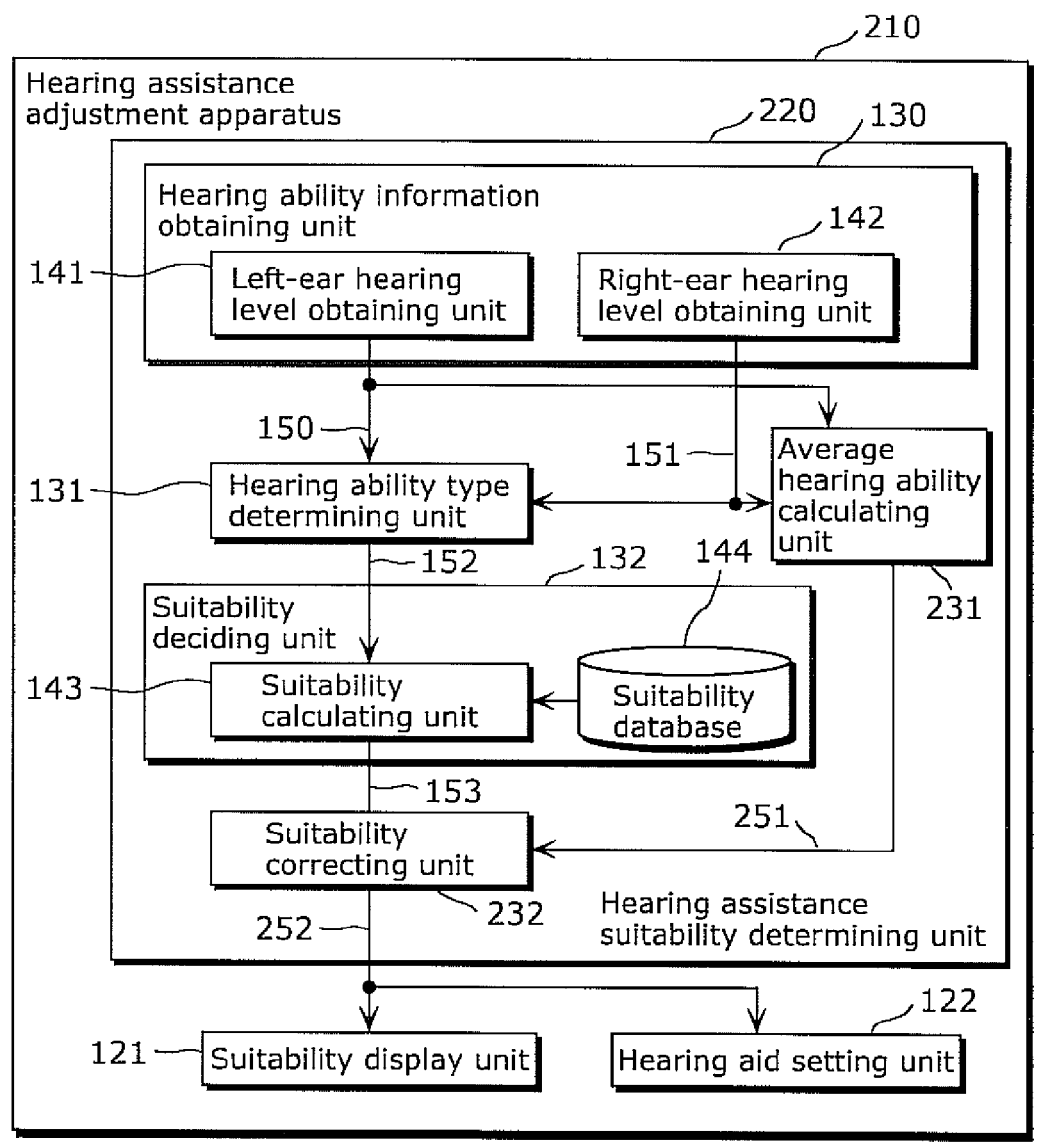
[FIG. 13]

FIG. 13 is a block diagram showing a hearing assistance adjustment device 210 according to Embodiment 2 of the present invention. It is to be noted that the same reference signs are assigned to the same elements as those of the hearing assistance adjustment device 110 according to Embodiment 1 shown in FIG. 5 and that the following mainly describes differences, and overlapping description is omitted.

The hearing assistance adjustment device 210 shown in FIG. 13 differs from the hearing assistance adjustment device 110 according to Embodiment 1 in a structure of a hearing assistance suitability determining device 220. More specifically, in addition to the structure of the hearing assistance suitability determining device 120, the hearing assistance suitability determining device 220 further includes: an average hearing level calculating unit 231 which calculates an average hearing level 251 of both of the left and right ears; and a suitability correcting unit 232 which generates a suitability 252 by correcting the suitability 153 according to the average hearing level 251.

Next, an operation of the hearing assistance adjustment device 210 is described.

Figure 14:
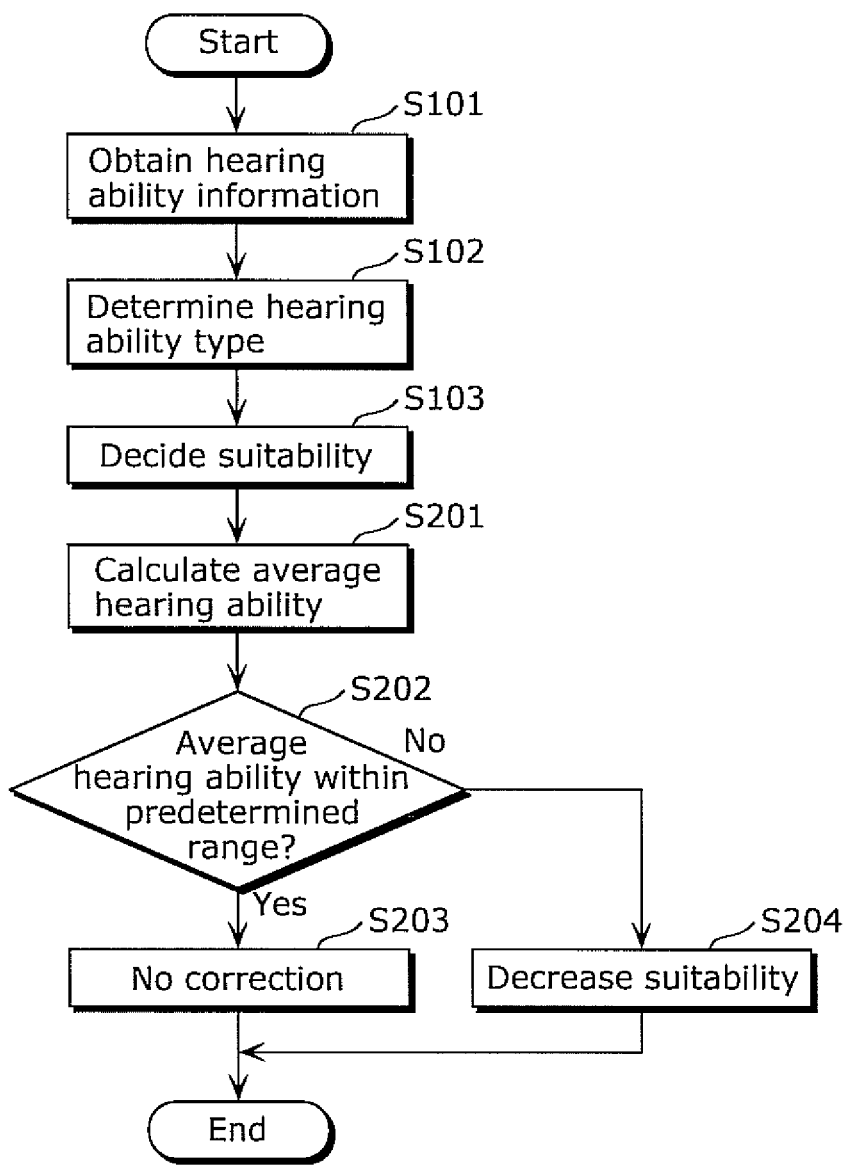
[FIG. 14]

FIG. 14 is a flowchart of a hearing assistance processing adjustment method performed by the hearing assistance adjustment device 210. It is to be noted that processes at the steps S101 to S103 are the same as in Embodiment 1.

The average hearing level calculating unit 231 calculates the average hearing level 251 which is an average value of hearing levels for frequencies which are indicated by hearing ability information (S201). In other words, the average hearing level calculating unit 231 calculates an overall hearing level, that is, a degree of parallel translation of an audiogram in a vertical direction.

For instance, the average hearing level calculating unit 231 may calculate a hearing level at a specific frequency as the average hearing level 251. Furthermore, the average hearing level calculating unit 231 may calculate, as the average hearing level 251, a value which is calculated by using three-way classification shown by Equation 7, quartation shown by Equation 8, or six-way classification shown by Equation. 9, and which is commonly used in the appropriate industry.

[Math. 7]

$$L_{ave} = \frac{L_{500} + L_{1000} + L_{2000}}{3}$$ (Equation 7)

[Math. 8]

$$L_{ave} = \frac{L_{500} + (L_{1000} \times 2) + L_{2000}}{4}$$ (Equation 8)

[Math. 9]

$$L_{ave} = \frac{L_{500} + (L_{1000} \times 2) + (L_{2000} \times 2) + L_{4000}}{6}$$ (Equation 9)

It is to be noted that $L_{500}$, $L_{1000}$, and $L_{4000}$ are hearing levels at frequencies 500 Hz, 1 kHz, 2 kHz, and 4 kHz, respectively.

Moreover, although a value which is obtained by averaging average hearing levels each of which is calculated for one of the left and right ears is used as a representative value here, it is acceptable to use the average hearing levels each of which is calculated for the one of the left and right ears.

Here, in the case where the hearing is hardly deteriorated or for extremely profound hearing loss, a sufficient improvement effect cannot be expected regardless of a hearing ability type even if the dichotic hearing assistance is performed. Thus, when the overall hearing level is outside of a certain range (No in S202), the suitability correcting unit 232 performs weighting so as to decrease the suitability 153 decided by the suitability deciding unit 132 (S204). For example, when the average hearing level is less than a lower limit or greater than an upper limit, the suitability correcting unit 232 sets the suitability 252 to 0. Furthermore, when the overall hearing level is within the certain range (Yes in S202), the suitability correcting unit 232 directly outputs the suitability 153 as the suitability 252 (S203).

Figure 15:
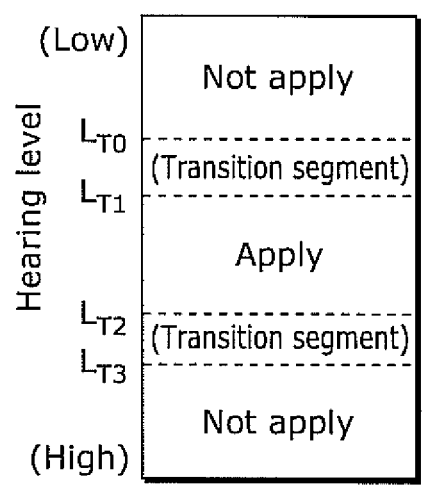
[FIG. 15]

Moreover, as shown in FIG. 15, the suitability correcting unit 232 may set thresholds (e.g., $L_{T0}$, $L_{T1}$, $L_{T2}$, $L_{T3}$) for the determination of the hearing level, and provide transition segments in each of which the average hearing level 251 is weighted to the determination of the suitability.

Figure 16:
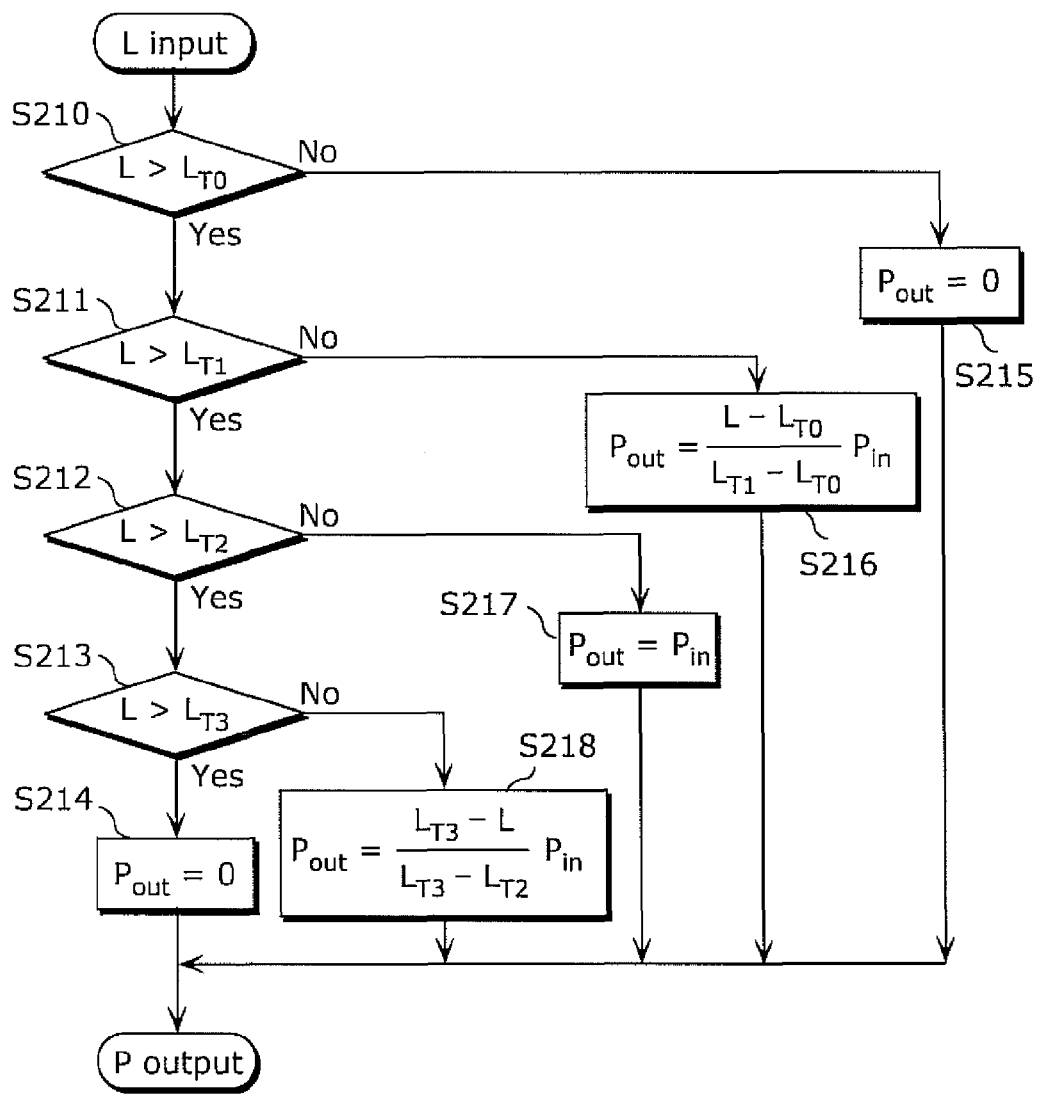
[FIG. 16]

FIG. 16 is a flowchart of an example of an algorithm of transition processing in this case.

It is to be noted that hearing levels $L_{T0}$ to $L_{T3}$ are assumed to increase in order of index number. Furthermore, L is the average hearing level 251, $P_{in}$ is the suitability 153 calculated by the suitability deciding unit 132, and $P_{out}$ is the suitability 252 corrected by the suitability correcting unit 232.

When the average hearing level 251 is lower than $L_{T0}$, that is, the hearing is hardly deteriorated (No in S210), the suitability correcting unit 232 determines that the dichotic hearing assistance is not to be applied, and sets the suitability 252 to 0 as shown in Equation 10.

Moreover, when the average hearing level 251 is between $L_{T0}$ and $L_{T1}$ (No in S211), the suitability correcting unit 232 performs linear transition processing by using Equation 11 (S216).

Furthermore, when the average hearing level 251 is between $L_{T1}$ and $L_{T2}$ (No in S212), the suitability correcting unit 232 uses, as the suitability 252, the suitability 153 calculated by the suitability calculating unit 143, as shown in Equation 12 (S217).

Moreover, when the average hearing level 251 is between $L_{T2}$ and $L_{T3}$ (No in S213), the suitability correcting unit 232 performs linear transition processing by using Equation 13 (S218).

Furthermore, when the average hearing level 251 is greater than $L_{T3}$, that is, in the case of the extremely profound hearing loss (Yes in S213), the suitability correcting unit 232 determines that the dichotic hearing assistance is not to be applied, and sets the suitability 252 to 0 as shown in Equation 10 (S214).

[Math. 10]
$$P_{out} = 0 \quad \text{(Equation 10)}$$

[Math. 11]
$$P_{out} = \frac{L - L_{T0}}{L_{T1} - L_{T0}} P_{in} \quad \text{(Equation 11)}$$

[Math. 12]
$$P_{out} = P_{in} \quad \text{(Equation 12)}$$

[Math. 13]
$$P_{out} = \frac{L_{T3} - L}{L_{T3} - L_{T2}} P_{in} \quad \text{(Equation 13)}$$

It is to be noted that when the average hearing level calculating unit 231 calculates an average hearing level of the hearing levels of each of the left and right ears, the suitability correcting unit 232 may perform weighting so as to decrease suitability when one of the average hearing levels is outside of the above range.

As described above, the hearing assistance adjustment device 210 according to Embodiment 2 of the present invention makes it possible to more adaptively perform the determination as to whether or not the dichotic hearing assistance is suitable for a user whose hearing deterioration is little or significant, and the setting of the dichotic hearing assistance, only by measuring the hearing levels of the user.

Moreover, although the above embodiment has described, as the example, the hearing assistance adjustment system 100, the hearing assistance adjustment device 210, and the hearing assistance processing adjustment method which make it possible to adjust the hearing assistance processing of the hearing aid, the present invention is not limited to this, and enables the similar determination and setting in other audio equipment.

Furthermore, the hearing assistance adjustment device 210 may include only one of the suitability display unit 121 and the hearing aid setting unit 122.

(Embodiment 3)

Embodiment 3 of the present invention describes a modification of the hearing assistance adjustment device 110 according to Embodiment 1. A hearing assistance adjustment device 310 according to Embodiment 3 of the present invention corrects a suitability according to a profile of a subject.

Figure 17:
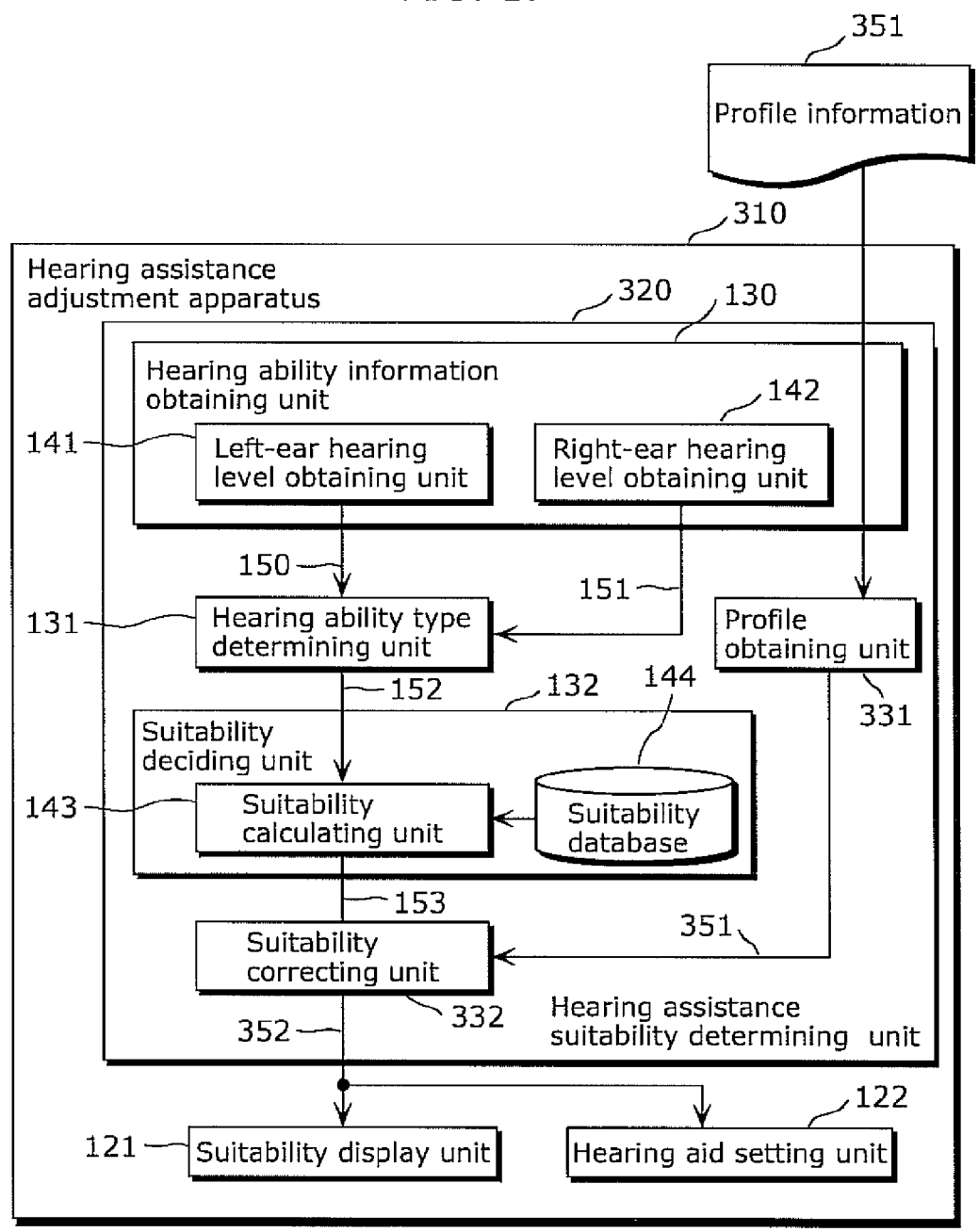
[FIG. 17]

FIG. 17 is a block diagram showing a hearing assistance adjustment device 310 according to Embodiment 3 of the present invention. It is to be noted that the same reference signs are assigned to the same elements as those of the hearing assistance adjustment device 110 according to Embodiment 1 shown in FIG. 5 and that the following mainly describes differences, and overlapping description is omitted.

The hearing assistance adjustment device 310 shown in FIG. 17 differs from the hearing assistance adjustment device 110 according to Embodiment 1 in a structure of a hearing assistance suitability determining device 320. More specifically, in addition to the structure of the hearing assistance suitability determining device 120, the hearing assistance suitability determining device 320 further includes a suitability correcting unit 332 and a profile obtaining unit 331 which obtains profile information 351 of a subject.

The profile obtaining unit 331 obtains the profile information 351 from an interface, a recording medium on which the profile information 351 is recorded, and so on. The profile information 351 indicates an age of the subject or a period of use which is a period in which the subject has used a hearing aid.

The suitability correcting unit 332 generates a suitability 352 by correcting the suitability 153 according to the profile information 351.

Next, an operation of the hearing assistance adjustment device 310 is described.

Figure 18:
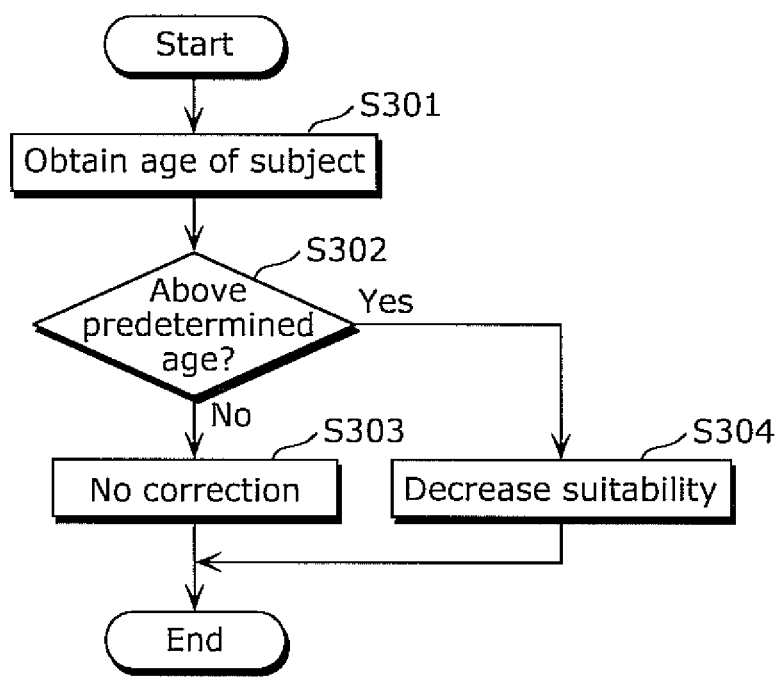
[FIG. 18]

FIG. 18 is a flowchart of suitability correction processing performed by the hearing assistance adjustment device 310 in the case where the profile information 351 includes information indicating the age of the subject. It is to be noted that the processes (the steps S101 to S103 in FIG. 6) until the suitability 153 is decided are the same as those in Embodiment 1.

Here, although the hearing impairment is caused by aging, since the brain functions deteriorate concurrently, considered is a possibility that words cannot be recognized even if the deterioration in hearing is compensated by hearing assistance.

In response to the above, the profile obtaining unit 331 obtains the profile information 351 indicating an index showing a condition of brain deterioration such as the age of the subject (S301).

When the age of the subject is equal to or higher than a predetermined age (e.g., 80 years old) (Yes in S302), the suitability correcting unit 332 considers that the brain deterioration has become advanced, and performs correction so as to decrease the suitability 153 (S304).

On the other hand, when the age of the subject is below the predetermined age (No in S302), the suitability correcting unit 332 directly outputs the suitability 153 as the suitability 352 (S303).

Figure 19:
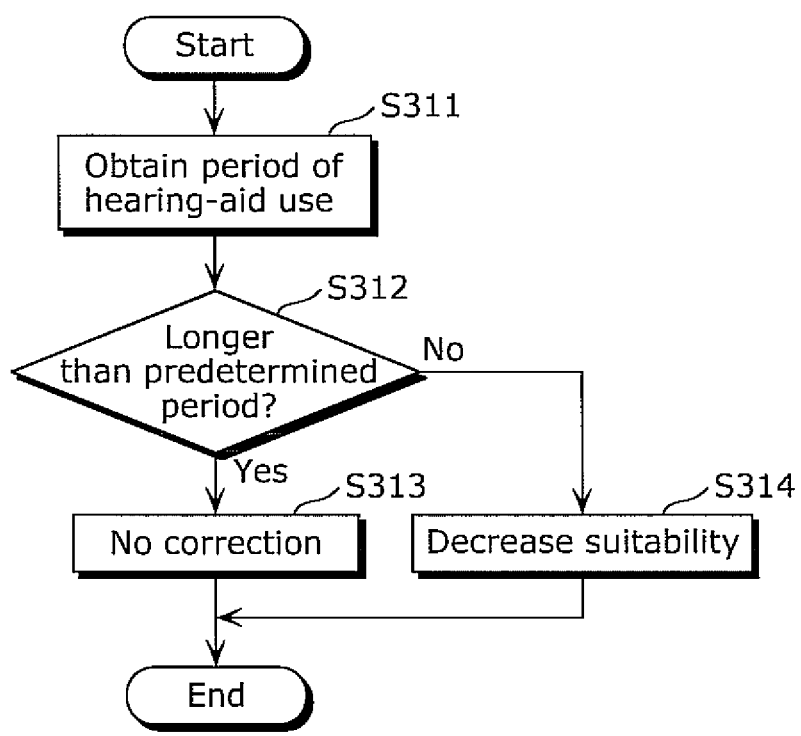
[FIG. 19]

FIG. 19 is a flowchart of suitability correction processing performed by the hearing assistance adjustment device 310 in the case where the profile information 351 includes information indicating a period of use which is a period in which the subject has used a hearing aid. It is to be noted that the period of use may be information directly indicating the period in which the subject has used the hearing aid or information indirectly indicating the period in which the subject has used the hearing aid, such as an age at which the subject wore the hearing aid for the first time.

Here, a hearing-aid user who is not sufficiently used to sound heard through the hearing aid generally tends to have a low sensitivity to differences in hearing assistance processing.

First, the profile obtaining unit 331 obtains the profile information 351 including the information indicating the period of use (S311).

When the period of use is shorter than a predetermined period (No in S312), the suitability correcting unit 332 performs correction so as to decrease the suitability 153 (S314).

On the other hand, when the period of use is longer than the predetermined period (Yes in S312), the suitability correcting unit 332 directly outputs the suitability 153 as the suitability 352 (S313).

It is to be noted that, here, the suitability display unit 121 may display not only the corrected suitability 352 as a suitability immediately after application but also the suitability 153 before correction as a suitability after the subject has sufficiently learned how to use the hearing aid.

As described above, the hearing assistance adjustment device 310 according to Embodiment 3 of the present invention makes it possible to more adaptively perform the determination as to whether or not the dichotic hearing assistance is suitable for the subject and the setting of the dichotic hearing assistance, only by using the profile information 351 of the user and measuring the hearing levels of the user.

Moreover, although the above embodiment has described, as the example, the hearing assistance adjustment system 100, the hearing assistance adjustment device 310, and the hearing assistance processing adjustment method which make it possible to adjust the hearing assistance processing of the hearing aid, the present invention is not limited to this, and enables the similar determination and setting in other audio equipment.

Furthermore, the suitability correcting unit 332 may provide thresholds for the determination of the age or the period of use, and set the transition segments as shown in FIG. 15.

Moreover, the hearing assistance adjustment device 310 may include only one of the suitability display unit 121 and the hearing aid setting unit 122.

(Embodiment 4)

Embodiment 4 of the present invention describes a modification of the hearing assistance adjustment device 110 according to Embodiment 1. A hearing assistance adjustment device 410 according to Embodiment 4 of the present invention corrects a suitability according to a difference between left- and right-hearing levels of a subject.

Figure 20:
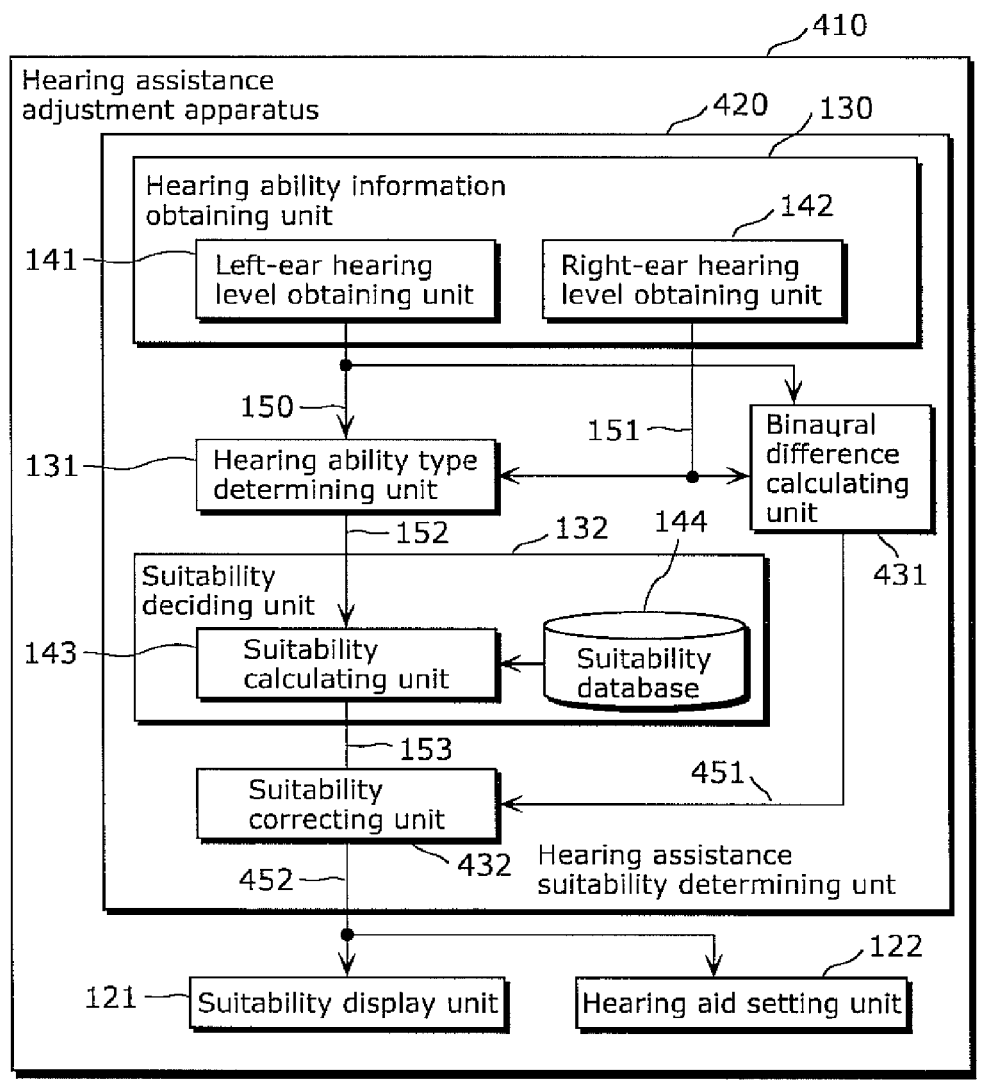
[FIG. 20]

FIG. 20 is a block diagram showing the hearing assistance adjustment device 410 according to Embodiment 4 of the present invention. It is to be noted that the same reference signs are assigned to the same elements as those of the hearing assistance adjustment device 110 according to Embodiment 1 shown in FIG. 5 and that the following mainly describes differences, and overlapping description is omitted.

The hearing assistance adjustment device 420 shown in FIG. 20 differs from the hearing assistance adjustment device 110 according to Embodiment 1 in a structure of a hearing assistance suitability determining device 420. More specifically, in addition to the structure of the hearing assistance suitability determining device 120, the hearing assistance suitability determining device 420 further includes a suitability correcting unit 432 and a binaural difference calculating unit 431 which calculates a difference between left- and right-hearing levels.

Figure 21:
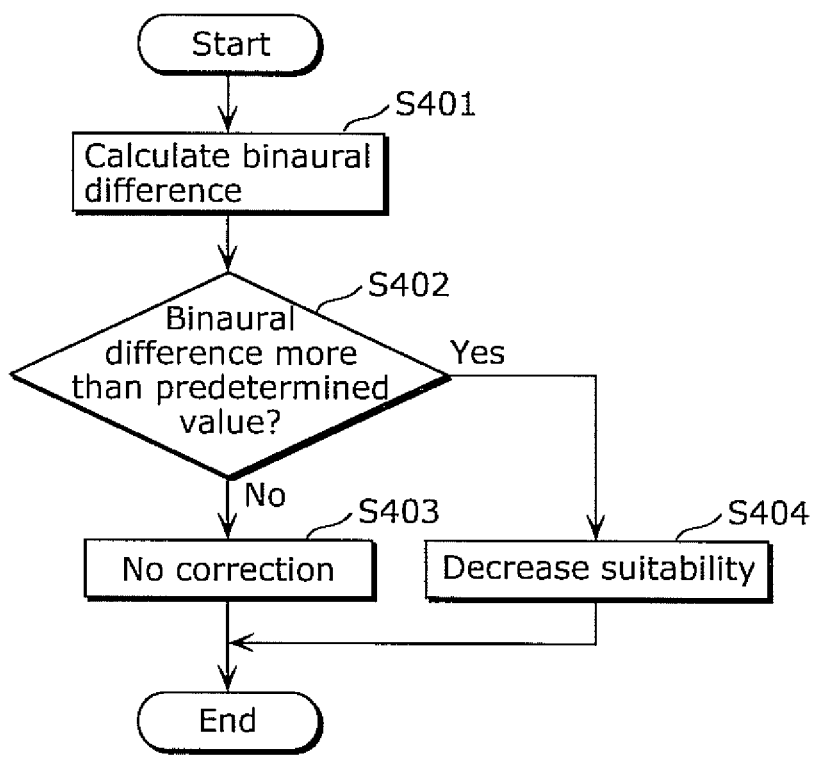
[FIG. 21]

FIG. 21 is a flowchart of a hearing assistance processing adjustment method performed by the hearing assistance adjustment device 410.

First, the binaural difference calculating unit 431 calculates a binaural difference 451 which is an absolute value of a difference between the hearing levels of the right ear indicated by the right-ear hearing ability information 151 and the hearing levels of the left ear indicated by the left-ear hearing ability information 150 (S401). More specifically, for instance, the binaural difference 451 is an absolute value of a difference between the right-ear average hearing level and the left-ear average hearing level. Furthermore, as with the average hearing level calculating unit 231 according to above-described Embodiment 2, the binaural difference calculating unit 431 may use the hearing level at the specific frequency as the average hearing level or use a value calculated using an equation such as three-way classification, quartation, and six-way classification as respectively indicated by above Equations 7 to 9 as the average hearing level.

When the binaural difference 451 is equal to or greater than a predetermined value (Yes in S402), the suitability correcting unit 432 performs correction so as to decrease the suitability 153 (S404).

On the other hand, when the binaural difference 451 is below the predetermined value (No in S402), the suitability correcting unit 432 directly outputs the suitability 153 as a suitability 452 (S403).

As described above, the hearing assistance adjustment device 410 according to Embodiment 4 of the present invention makes it possible to more adaptively perform the determination as to whether or not the dichotic hearing assistance is suitable for the user whose auditory characteristics of the left and right ears are different from each other, and the setting of the dichotic hearing assistance, only by measuring the hearing levels of the user.

Moreover, although the above embodiment has described, as the example, the hearing assistance adjustment system 100, the hearing assistance adjustment device 410, and the hearing assistance processing adjustment method which make it possible to adjust the hearing assistance processing of the hearing aid, the present invention is not limited to this, and enables the similar determination and setting in other audio equipment.

Furthermore, the suitability correcting unit 432 may provide thresholds for the determination of the binaural difference 451, and set the transition segments as shown in FIG. 15.

Moreover, the hearing assistance adjustment device 410 may include only one of the suitability display unit 121 and the hearing aid setting unit 122.

(Embodiment 5)

Embodiment 5 of the present invention describes a modification of the hearing assistance adjustment device 110 according to Embodiment 1. A hearing assistance adjustment device 510 according to Embodiment 5 of the present invention further determines which of left and right ears a high tone is to be assigned to in dichotic hearing assistance.

Figure 22:
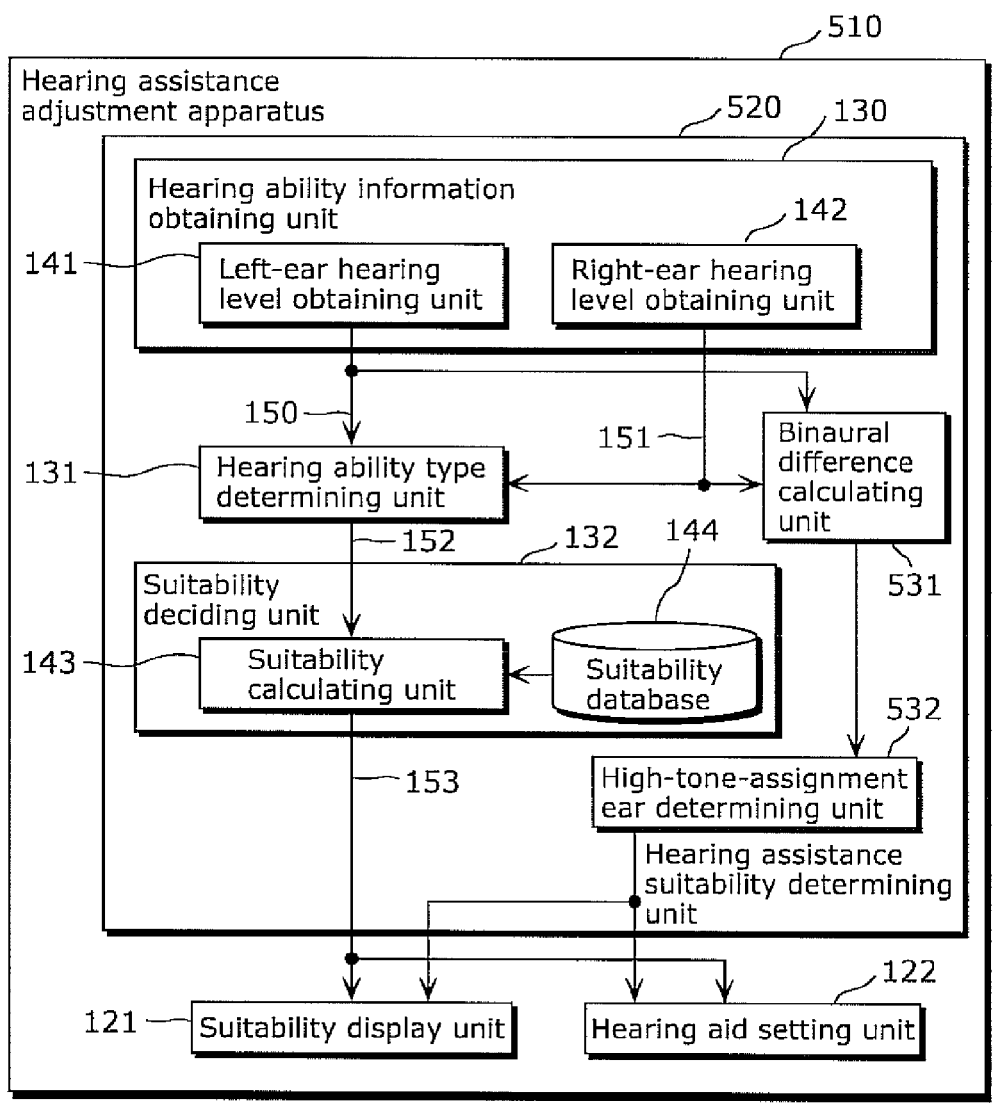
[FIG. 22]

FIG. 22 is a block diagram showing the hearing assistance adjustment device 510 according to Embodiment 5 of the present invention. It is to be noted that the same reference signs are assigned to the same elements as those of the hearing assistance adjustment device 110 according to Embodiment 1 shown in FIG. 5 and that the following mainly describes differences, and overlapping description is omitted.

The hearing assistance adjustment device 510 shown in FIG. 22 differs from the hearing assistance adjustment device 110 according to Embodiment 1 in a structure of a hearing assistance suitability determining device 520. More specifically, in addition to the structure of the hearing assistance suitability determining device 120, the hearing assistance suitability determining device 520 further includes: a binaural difference calculating unit 531 which calculates a difference between the left- and right-hearing levels; and a high-tone-assignment ear determining unit 532 which determines which of the left and right ears a high tone is to be assigned to, based on the difference between the left- and right-hearing levels.

The binaural difference calculating unit 531 calculates a difference regarding frequency characteristics of left-ear and right-ear hearing levels. More specifically, the binaural difference calculating unit 531 calculates a high tone hearing level difference which is a left-ear and right-ear hearing level difference at a frequency (high tone) higher than the crossover frequency fc, and a low tone hearing level difference which is a left-ear and right-ear hearing level difference at a frequency (low tone) lower than the crossover frequency fc. It is to be noted that when calculating the high tone hearing level difference and the low tone hearing level difference, the binaural difference calculating unit 531 may use a hearing level at a representative frequency such as 2 kHz and 500 Hz or an average value of hearing levels at frequencies.

Figure 23:
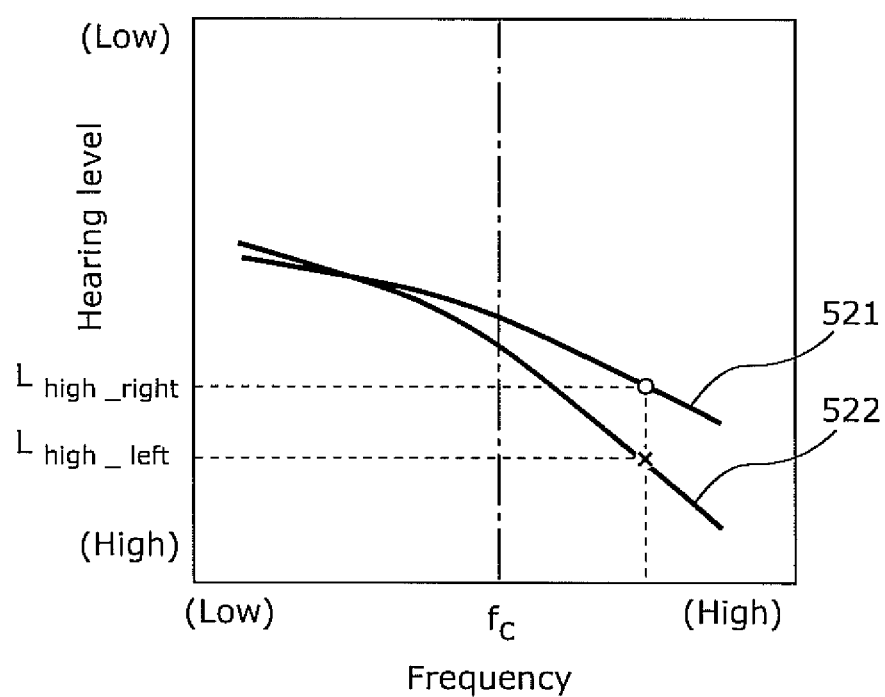
[FIG. 23]

The following describes, as an example, an audiogram, for instance, as shown in FIG. 23. It is to be noted that the horizontal axis in FIG. 23 indicates a frequency, and fc indicates a crossover frequency. Furthermore, the vertical axis in FIG. 23 indicates a hearing level. A right-ear hearing level 521 is lower than a left-ear hearing level 522 at a frequency higher than the crossover frequency. Accordingly, the high-tone-assignment ear determining unit 532 determines that the right ear has a less deterioration in high tone hearing.

Figure 24:
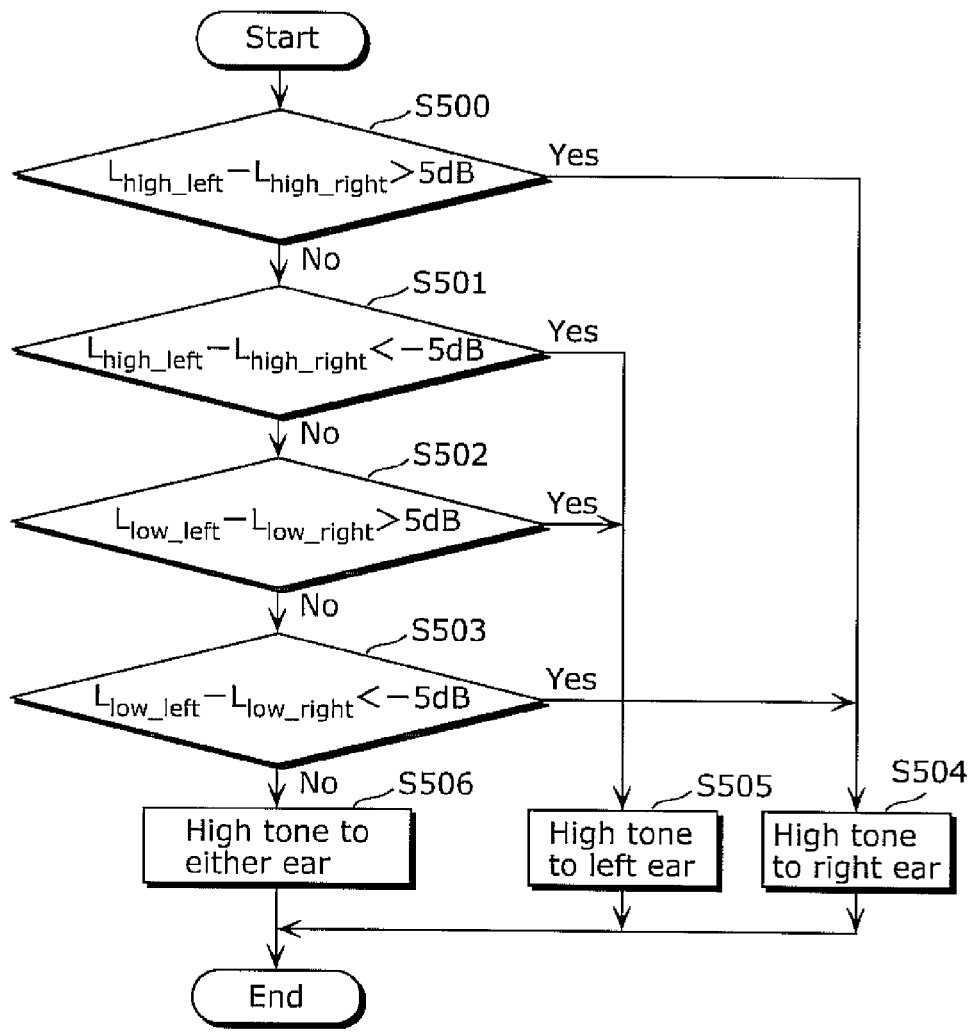
[FIG. 24]

FIG. 24 is a flowchart showing an example of an algorithm of determination processing performed by the high-tone-assignment ear determining unit 532.

First, when a high tone hearing ability of the right ear is equal to or greater than a predetermined value in comparison with a high tone hearing ability of the left ear ($L_{high\_left}$ which is a high tone hearing level of the left ear is equal to or greater than the predetermined value (e.g., 5 dB) in comparison with $L_{high\_right}$ which is a high tone hearing level of the right ear) (Yes in S500), the high-tone-assignment ear determining unit 532 decides to assign the high tone to the right ear, and the low tone to the left ear (S504).

Next, when the high tone hearing ability of the left ear is equal to or greater than a predetermined value ($L_{high\_right}$ is equal to or greater than the predetermined value (e.g., 5 dB) in comparison with $L_{high\_left}$) (Yes in S501), the high-tone-assignment ear determining unit 532 decides to assign the high tone to the left ear, and the low tone to the right ear (S505).

Moreover, where a significant difference (e.g., the difference of ±5 dB or more) between the left and right ears for the high tone is not observed (No in S500 and No in S501), the high-tone-assignment ear determining unit 532 further performs the determination processing using a low tone hearing level.

More specifically, when a low tone hearing ability of the right ear is equal to or greater than a predetermined value in comparison with a low tone hearing ability of the left ear ($L_{low\_left}$ which is a low tone hearing level of the left ear is equal to or greater than the predetermined value (e.g., 5 dB) in comparison with $L_{low\_right}$ which is a low tone hearing level of the right ear) (Yes in S502), the high-tone-assignment ear determining unit 532 decides to assign the high tone to the left ear, and the low tone to the right ear (S505).

Furthermore, when the low tone hearing ability of the left ear is equal to or greater than a predetermined value in comparison with the low tone hearing ability of the right ear ($L_{low\_right}$ is equal to or greater than the predetermined value (e.g., 5 dB) in comparison with (Yes in S503), the high-tone-assignment ear determining unit 532 decides to assign the high tone to the right ear, and the low tone to the left ear (S504).

Moreover, when a significant difference is not observed for both the high and low tones (No in all of S500 to 503), the high-tone-assignment ear determining unit 532 decides to assign the high tone to either ear (S506).

Furthermore, the suitability display unit 121 displays a determination result by the high-tone-assignment ear determining unit 532, in addition to the suitability 153.

It is to be noted that the suitability display unit 121 may display both a suitability when the high tone is assigned to the right ear and a suitability when the high tone is assigned to the left ear. Moreover, the suitability display unit 121 may display an ear of which high tone hearing level is lower as a high-tone-assigned ear, and only a suitability when the high tone is assigned to the ear.

It is to be noted that the suitability display unit 121 may display a text or an icon in a color of a red color system when the high tone is assigned to the right ear, and display a text or an icon in a color of a blue color system or a green color system, or in a black color, when the high tone is assigned to the left ear. This makes it easier for a user of the hearing assistance adjustment device 510 to understand which of the left and right ears the high tone should be assigned to.

Furthermore, the hearing aid setting unit 122 sets a hearing aid according to, for example, the determination result by the high-tone-assignment ear determining unit 532.

As described above, the hearing assistance adjustment device 510 according to Embodiment 5 of the present invention makes it possible to more adaptively perform the determination as to whether or not the dichotic hearing assistance is suitable for the user, and the setting of the dichotic hearing assistance, only by measuring the hearing levels of the user. Moreover, although the above embodiment has described, as the example, the hearing assistance adjustment system 100, the hearing assistance adjustment device 510, and the hearing assistance processing adjustment method which make it possible to adjust the hearing assistance processing of the hearing aid, the present invention is not limited to this, and enables the similar determination and setting in other audio equipment.

Moreover, the hearing assistance adjustment device 510 may include only one of the suitability display unit 121 and the hearing aid setting unit 122.

(Embodiment 6)

Embodiment 6 of the present invention describes a hearing assistance adjustment device 610 which determines which of left and right ears a high tone is to be assigned to in dichotic hearing assistance, using a method different from the method described in Embodiment 5.

Figure 25:
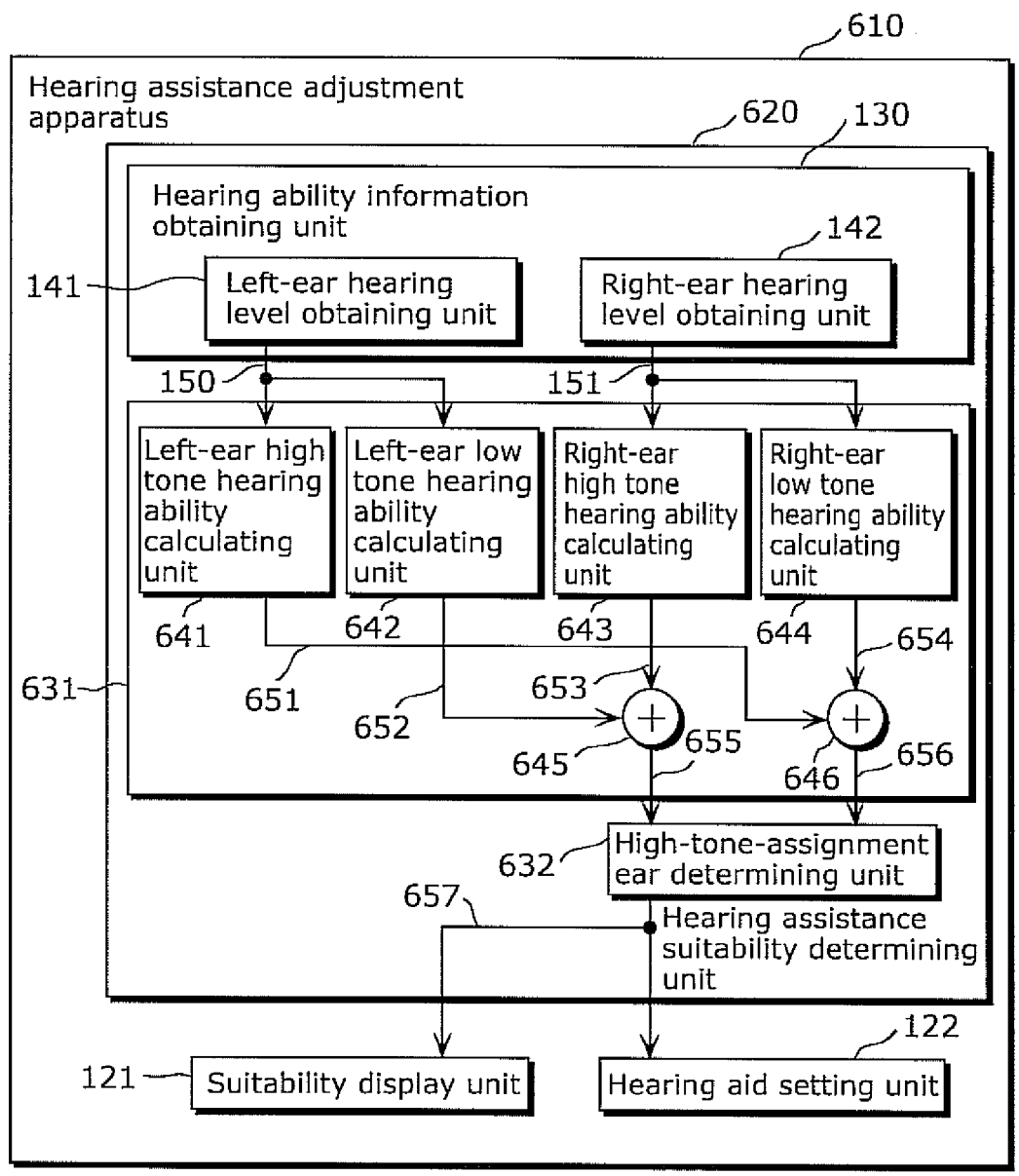
[FIG. 25]

FIG. 25 is a block diagram showing the hearing assistance adjustment device 610 according to Embodiment 6 of the present invention. It is to be noted that the same reference signs are assigned to the same elements as those of the hearing assistance adjustment device 110 according to Embodiment 1 shown in FIG. 5 and that the following mainly describes differences, and overlapping description is omitted.

The hearing assistance adjustment device 610 shown in FIG. 25 differs from the hearing assistance adjustment device 110 according to Embodiment 1 in a structure of a hearing assistance suitability determining device 620. More specifically, in addition to the structure of the hearing assistance suitability determining device 120, the hearing assistance suitability determining device 620 further includes a hearing ability calculating unit 631 and a high-tone-assignment ear determining unit 632. It is to be noted that though not illustrated in FIG. 25, the hearing assistance suitability determining device 620 may include the hearing ability type determining unit 131 and the suitability deciding unit 132 shown in FIG. 5.

The hearing ability calculating unit 631 includes: a left-ear high tone hearing ability calculating unit 641; a left-ear low tone hearing ability calculating unit 642; a right-ear high tone hearing ability calculating unit 643; a right-ear low tone hearing ability calculating unit 644; a first adding unit 645; and a second adding unit 646.

The left-ear high tone hearing ability calculating unit 641 calculates a left-ear high tone hearing level 651 which is a hearing level in a frequency range higher than a crossover frequency fc in the left-ear hearing ability information 150.

The left-ear low tone hearing ability calculating unit 642 calculates a left-ear low tone hearing level 652 which is a hearing level in a frequency range lower than the crossover frequency fc in the left-ear hearing ability information 150.

The right-ear high tone hearing ability calculating unit 643 calculates a right-ear high tone hearing level 653 which is a hearing level in the frequency range higher than the crossover frequency fc in the right-ear hearing ability information 151.

The right-ear low tone hearing ability calculating unit 644 calculates a right-ear low tone hearing level 654 which is a hearing level in the frequency range lower than the crossover frequency fc in the right-ear hearing ability information 151.

The first adding unit 645 calculates a first addition hearing level 655 by adding up the left-ear low tone hearing level 652 and the right-ear high tone hearing level 653.

The second adding unit 646 calculates a second addition hearing level 656 by adding up the left-ear high tone hearing level 651 and the right-ear low tone hearing level 654.

The high-tone-assignment ear determining unit 632 determines, using the first addition hearing level 655 and the second addition hearing level 656, which of the left and right ears high-tone components are to be assigned to at the time of providing dichotic hearing assistance, and outputs high-tone-assigned-ear information 657 indicating the determination result.

The suitability display unit 121 notifies a user of the determination result indicated by the high-tone-assigned-ear information 657.

The hearing aid setting unit 122 changes settings of a hearing aid according to the determination result indicated by the high-tone-assigned-ear information 657.

Figure 26:
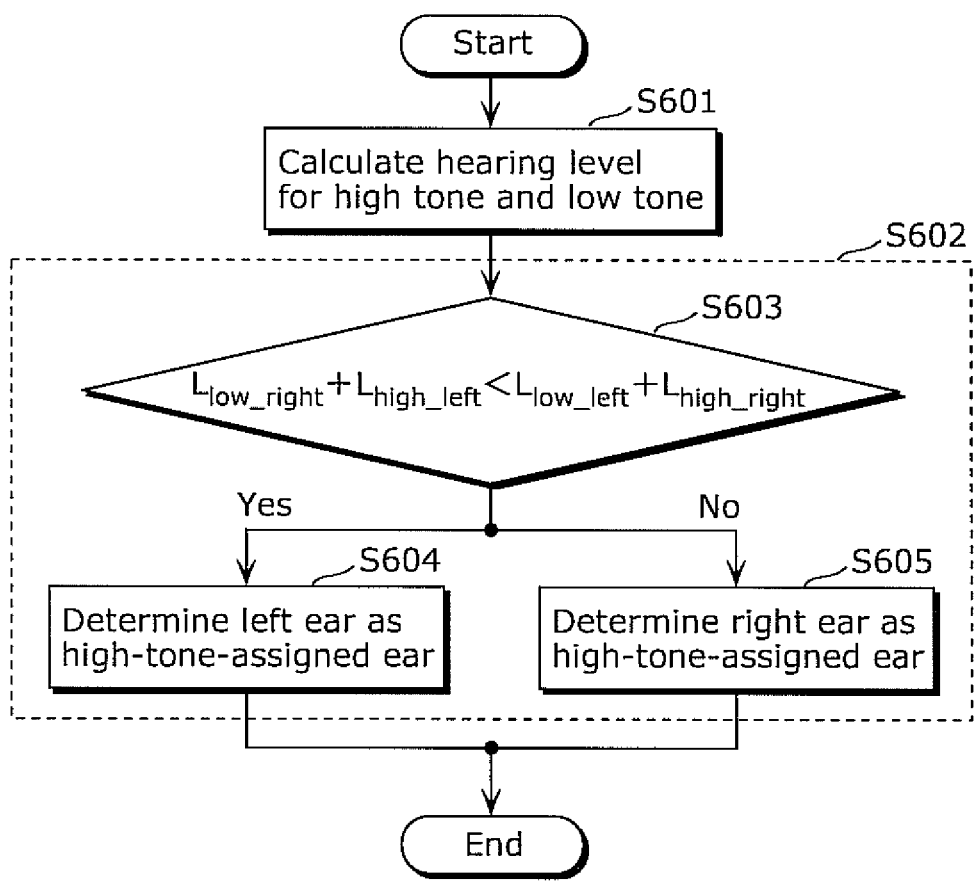
[FIG. 26]

Next, an operation of the hearing assistance adjustment device 610 is described with reference to FIG. 26. It is to be noted that in FIG. 26, $L_{high\_left}$ indicates the left-ear high tone hearing level 651, $L_{low\_left}$ indicates the left-ear low tone hearing level 652, $L_{high\_right}$ indicates the right-ear high tone hearing level 653, and $L_{low\_right}$ indicates the right-ear low tone hearing level 654.

First, the hearing ability calculating unit 631 calculates, from the left-ear hearing ability information 150 and the right-ear hearing ability information 151, the left-ear high tone hearing level 651, the left-ear low tone hearing level 652, the right-ear high tone hearing level 653, and the right-ear low tone hearing level 654 (S601). It is to be noted that the left-ear high tone hearing level 651, the left-ear low tone hearing level 652, the right-ear high tone hearing level 653, and the right-ear low tone hearing level 654 may be calculated in any order or in parallel.

Here, the hearing ability calculating unit 631 may use, as a representative value, a hearing level at a specific frequency higher (or lower) than the crossover frequency fc as a high tone (or low tone) hearing ability or use, as a representative value, an average value of hearing levels at frequencies in a band higher (or lower) than the crossover frequency fc. Alternatively, it is possible to limit the hearing level, which is used as the representative value, to a hearing level at a frequency that is ⅓ or more octave away from the crossover frequency fc. This is because using measurement results at frequencies at a fixed distance or more makes it possible to more accurately measure a hearing ability of the user in a high frequency range, since hearing levels near the crossover frequency fc influence both sonority of vowels at a masking side and sonority of consonants at a side to be masked.

Next, the hearing assistance adjustment device 610 determines an ear to which a high-frequency audio signal is to be assigned, based on, among combinations of high tone hearing levels and low tone hearing levels, a combination in which the sum of the hearing levels is high (S602).

More specifically, the hearing ability calculating unit 631 calculates the second addition hearing level 656 by adding up the left-ear high tone hearing level 651 and the right-ear low tone hearing level 654, and outputs the second addition hearing level 656 to the high-tone-assignment ear determining unit 632. The second addition hearing level 656 is an index indicating a hearing ability of sound when, through the dichotic hearing assistance, the high tone is assigned to a left ear of a listener and the low tone is assigned to a right ear of the listener (hereinafter, referred to as a left-high-tone hearing ability). It is to be noted that the lower the second addition hearing level 656 is, the better the left-high-tone hearing ability is.

Furthermore, the hearing ability calculating unit 631 calculates the first addition hearing level 655 by adding up the right-ear high tone hearing level 653 and the left-ear low tone hearing level 652, and outputs the first addition hearing level 655 to the high-tone-assignment ear determining unit 632. The first addition hearing level 655 is an index indicating a hearing ability of sound when, through the dichotic hearing assistance, the high tone is assigned to the right ear of the listener and the low tone is assigned to the left ear of the listener (hereinafter, referred to as a right-high-tone hearing ability). It is to be noted that the lower the first addition hearing level 655 is, the better the right-high-tone hearing ability is.

The high-tone-assignment ear determining unit 632 compares the left-high-tone hearing ability and the right-high-tone hearing ability according to the first addition hearing level 655 and the second addition hearing level 656 (S603).

When the second addition hearing level 656 is lower than the first addition hearing level 655 (the left-high-tone hearing ability is better than the right-high-tone hearing ability) (Yes in S603), that is, when the listener hears sound better at the time when the high tone is assigned to the left ear than at the time when the high tone is assigned to the right ear, the high-tone-assignment ear determining unit 632 determines the left ear as a high-tone-assigned ear (S604).

Moreover, when the second addition hearing level 656 is higher than the first addition hearing level 655 (the left-high-tone hearing ability is better than the right-high-tone hearing ability) (No in S603), that is, when the listener hears sound better at the time when the high tone is assigned to the right ear than at the time when the high tone is assigned to the left ear, the high-tone-assignment ear determining unit 632 determines the right ear as the high-tone-assigned ear (S605).

After performing the determination of the dichotic hearing assistance in the above manner, the high-tone-assignment ear determining unit 632 outputs, to either the suitability display unit 121 or the hearing aid setting unit 122, the high-tone-assigned-ear information 657 which indicates the determined high-tone-assigned ear.

The suitability display unit 121 may display the high-tone-assigned ear in text on a screen of the hearing assistance adjustment device 610, in icon shape or by color on the screen, or with a lamp.

The hearing aid setting unit 122 may notify the left-ear hearing aid 103 and the right-ear hearing aid 104 of the determined high-tone-assigned ear or a gain for amplifying each band.

The following describes in detail an example operation regarding the determination of the dichotic hearing assistance. Here, the crossover frequency fc is assumed to be 800 Hz. It is also assumed that the left-ear high tone hearing ability calculating unit 641 and the right-ear high tone hearing ability calculating unit 643 output a hearing level at 2000 Hz as a representative value, and that the left-ear low tone hearing ability calculating unit 642 and the right-ear low tone hearing ability calculating unit 644 output a hearing level at 250 Hz as a representative value. Furthermore, an operation for setting the dichotic hearing assistance for a hearing-impaired person having the hearing ability shown in FIG. 3 is described.

The left-ear hearing level obtaining unit 141 obtains, from the audiometer 101, the hearing level at each frequency shown in the left-ear column in FIG. 3. Likewise, the right-ear hearing level obtaining unit 142 obtains, from the audiometer 101, the hearing level at each frequency shown in the right-ear column in FIG. 3.

The left-ear high tone hearing ability calculating unit 641 extracts the value of 55 dB as the left-ear hearing level at 2000 Hz, the right-ear low tone hearing ability calculating unit 644 extracts the value of 40 dB as the right-ear hearing level at 250 Hz, the left-ear low tone hearing ability calculating unit 642 extracts the value of 30 dB as the left-ear hearing level at 250 Hz, and the right-ear high tone hearing ability calculating unit 643 extracts the value of 50 dB as the right-ear hearing level at 2000 Hz.

FIG. 27 shows results of clinical tests on 16 hearing-impaired people. The hearing-impaired person described in FIG. 3 corresponds to the fourth subject in FIG. 27.

In FIG. 27, column A shows reference numbers and left and right ears of the subjects, and column B shows a hearing level at each frequency measured by the audiometer 101. Moreover, column C shows, for each crossover frequency, a degree of clarity improvement by dichotic hearing assistance which is measured through each clinical test, column D shows a left-high-tone hearing ability for assigned bands and a right-high-tone hearing ability for assigned bands, and column E shows results of determination of a high-tone-assigned ear by the hearing assistance adjustment device 610. Furthermore, column F shows high-tone-assigned ears which have a higher degree of clarity improvement in the clinical tests, and column G shows circles when the determination results by the hearing assistance adjustment device match the results of the clinical tests and cross marks when they are different from each other. Moreover, columns E and F show L when the high-tone-assigned ear is the left ear and R when the high-tone-assigned ear is the right ear.

In the clinical tests, a sound that is produced when each of a man and a woman who have speech training experience utters a total of 40 types of syllables composed of five types of preceding vowels (the Japanese vowels: a, i, u, e, and o) and eight types of subsequent sounds (Japanese words: pa, ta, ka, ba, da, ga, sa, and za) is used as a test speech sound, an input signal is divided into high frequency/low frequency ranges to be assigned to the ears of the subjects, and the subjects are instructed to write down exactly what they heard on an answer sheet. A probability (accuracy rate) that the answered speech sound and the actual test speech sound match each other is the clarity.

The following describes the above fourth subject as an example with reference to FIG. 27. As shown by column D in FIG. 27, a left-high-tone hearing ability, which is one of inputs of the high-tone-assignment ear determining unit 632, is the sum of an output of the left-ear high tone hearing ability calculating unit 641 and an output of the right-ear low tone hearing ability calculating unit 644, and thus is indicated by 95 dB. On the other hand, a right-high-tone hearing ability, which is the other one of the inputs of the high-tone-assignment ear determining unit 632, is the sum of an output of the left-ear low tone hearing ability calculating unit 642 and an output of the right-ear high tone hearing ability calculating unit 643, and thus is indicated by 80 dB.

As shown by column E, the high-tone-assignment ear determining unit 632 compares 95 dB and 80 dB, and determines that it is desirable to assign the high tone to the right ear and the low tone to the left ear when performing the dichotic hearing assistance, because an input having a smaller value is the right-high-tone hearing ability.

Taking a case where the crossover frequency is 800 Hz as an example, for the fourth subject, while the clarity is reduced by 1% when the high tone is assigned to the left ear in comparison with a case where the dichotic hearing assistance is not performed, the clarity is improved by 13% when the high tone is assigned to the right ear in comparison with the case where the dichotic hearing assistance is not performed. Thus, it is verified that the determination result shown by column E matches the clinical evaluation result shown by column F. Furthermore, as shown by column G, it is verified that the method for determining the high-tone-assigned ear according to Embodiment 6 of the present invention is effective for the other subjects.

As stated above, the hearing assistance adjustment device 610 according to Embodiment 6 of the present invention makes it possible to set the high-tone-assigned ear in the dichotic hearing assistance that is effective for the subject, by only measuring the hearing levels of the subject. Moreover, although the above embodiment has described, as the example, the hearing assistance adjustment system 100, the hearing assistance adjustment device 610, and the hearing assistance processing adjustment method which make it possible to adjust the hearing assistance processing of the hearing aid, the present invention is not limited to this, and enables similar determination and setting in other audio equipment.

Moreover, the hearing assistance adjustment device 610 may include only one of the suitability display unit 121 and the hearing aid setting unit 122.

(Other Modifications)

It is to be noted that although the present invention has been explained based on the above embodiments, the present invention is certainly not limited to the embodiments. The present invention includes the following cases.

(1) Each of the above devices may be specifically a computer system including a micro processing unit, a ROM, a RAM, a hard disk unit, a display unit, a keyboard, a mouse, and the like. A computer program is stored in the RAM or the hard disk unit. The micro processing unit operates according to the computer program, so that each device fulfills its functions. Here, in order to fulfill predetermined functions, the computer program is programmed by combining instruction codes each of which indicates an instruction for a computer.

(2) Part or all of the components included in each of the above devices may be included in one system LSI (Large Scale Integration). The system LSI is a super-multifunctional LSI manufactured by integrating components into one chip, and is specifically a computer system including a micro processing unit, a ROM, a RAM, and the like. A computer program is stored in the RAM. The micro processing unit operates according to the computer program, so that the system LSI fulfills its functions.

(3) Part or all of the components included in each of the above devices may be in form of an IC card detachable from each device or in form of a single module. The IC card or module is a computer system including a micro processing unit, a ROM, a RAM, and the like. The IC card or module may include the above super-multifunctional LSI. The micro processing unit operates according to a computer program, so that the IC card or module fulfills its functions. The IC card or module may have tamper resistance.

(4) The present invention may be a method described above. Furthermore, the present invention may be a computer program which causes a computer to execute the method or may be a digital signal of the computer program.

Moreover, the present invention may be a computer-readable recording medium on which the computer program or digital signal is recorded. The computer-readable recording medium is, for instance, a flexible disk, a hard disk, a CD-ROM, an MO, a DVD, a DVD-ROM, a DVD-RAM, a BD (Blu-ray Disc), and a semiconductor memory. The present invention may also be the digital signal recorded on the recording medium.

Furthermore, the present invention may be transmission of the computer program or digital signal via a network represented by a telecommunication line, a wired or wireless communication line, and the Internet, or data broadcasting, etc.

Moreover, the present invention may be a computer system including a memory in which the above computer program is stored and a micro processing unit which operates according to the computer program.

Furthermore, the program or digital signal may be recorded on the recording medium and then transmitted, or the program or digital signal may be transmitted via the network or the like, so that the present invention can be implemented by another independent computer system.

(5) The above embodiments and the above modifications may be combined.

[Industrial Applicability]

The present invention is generally useful for hearing aids, audio systems, mobile phones, and apparatuses which performs speech reproduction and verbal communication such as public address.

REFERENCE SIGNS LIST 100, 900 Hearing assistance adjustment system
101, 901 Audiometer
102, 902 Headphones
103 Left-ear hearing aid
104 Right-ear hearing aid
110, 210, 310, 410, 510, 610, 910 Hearing assistance adjustment device
120, 220, 320, 420, 520, 620, 920 Hearing assistance suitability determining device
121 Suitability display unit
122, 914 Hearing aid setting unit
130 Hearing ability information obtaining unit
131 Hearing ability type determining unit
132 Suitability deciding unit
141 Left-ear hearing level obtaining unit
142 Right-ear hearing level obtaining unit
143 Suitability calculating unit
144 Suitability database
150 Left-ear hearing ability information
151 Right-ear hearing ability information
152 Hearing ability type
153, 252, 352, 452 Suitability
180 Suitability display region
181 Screen
182 Probability for effectiveness display region
183 Average amount of improvement display region
184 Determination standard input field
185 High-tone-assigned ear input field
186 Crossover frequency input field
187 Button 231 Average hearing level calculating unit
232, 332, 432 Suitability correcting unit
251 Average hearing level
331 Profile obtaining unit
351 Profile information
431, 531 Binaural difference calculating unit
451 Binaural difference
521 Right-ear hearing level
522 Left-ear hearing level
532, 632 High-tone-assignment ear determining unit
631 Hearing ability calculating unit
641 Left-ear high tone hearing ability calculating unit
642 Left-ear low tone hearing ability calculating unit
643 Right-ear high tone hearing ability calculating unit
644 Right-ear low tone hearing ability calculating unit
645 First adding unit
646 Second adding unit
651 Left-ear high tone hearing level
652 Left-ear low tone hearing level
653 Right-ear high tone hearing level
654 Right-ear low tone hearing level
655 First addition hearing level
656 Second addition hearing level
657 High-tone-assigned-ear information
903 Hearing aid
911 Hearing level obtaining unit
912 Amplification amount calculating unit
913 Amplification amount display unit
951 Auditory filter measuring unit
952 Frequency resolution calculating unit

The invention claimed is:

1. A hearing assistance suitability determining device which determines a suitability of a subject for dichotic hearing assistance, said hearing assistance suitability determining device comprising:

a hearing ability information obtaining unit configured to obtain hearing ability information indicating a hearing ability of the subject for frequencies;

a hearing ability type determining unit configured to determine, among hearing ability types each of which is defined by a tendency in a change of the hearing ability with respect to the frequencies, a hearing ability type of the hearing ability indicated by the hearing ability information; and a suitability deciding unit configured to decide, with reference to a table, the suitability of the subject for the dichotic hearing assistance based on a suitability corresponding, in the table, to the hearing ability type determined by said hearing ability type determining unit, the table showing a correspondence relationship between each of the hearing ability types and one of suitabilities for dichotic hearing assistance, wherein one of the hearing ability types is a high-frequency sloping type in which a hearing ability decreases as a frequency becomes higher, and said suitability deciding unit is configured to decide that the suitability of the subject for the dichotic hearing assistance when the hearing ability type determined by said hearing ability type determining unit is the high-frequency sloping type is to be higher than the suitability when the hearing ability type determined by said hearing ability type determining unit is not the high-frequency sloping type.

2. The hearing assistance suitability determining device according to claim 1, wherein one of the hearing ability types is a high-frequency plunging type, said hearing ability type determining unit is configured to determine that the hearing ability type of the hearing ability is the high-frequency plunging type, when a decrement of the hearing ability in a frequency range higher than a predetermined frequency is greater than a predetermined first threshold, and said suitability deciding unit is configured to decide that the suitability of the subject for the dichotic hearing assistance when the hearing ability type determined by said hearing ability type determining unit is the high-frequency plunging type is to be lower than the suitability when the hearing ability type determined by said hearing ability type determining unit is the high-frequency sloping type.

3. The hearing assistance suitability determining device according to claim 2, wherein one of the hearing ability types is a flat type, said hearing ability type determining unit is configured to determine that the hearing ability type of the hearing ability is the flat type, when an amount of change of the hearing ability in all the frequencies indicated by the hearing ability information is smaller than a predetermined second threshold, and said suitability deciding unit is configured to decide that the suitability of the subject for the dichotic hearing assistance when the hearing ability type determined by said hearing ability type determining unit is the flat type is to be lower than the suitability when the hearing ability type determined by said hearing ability type determining unit is the high-frequency sloping type, and is to be higher than the suitability when the hearing ability type determined by said hearing ability type determining unit is the high-frequency plunging type.

4. The hearing assistance suitability determining device according to claim 3, wherein one of the hearing ability types is a chevron type in which the hearing ability increases and then decreases as the frequency becomes higher, and said suitability deciding unit is configured to decide that the suitability of the subject for the dichotic hearing assistance when the hearing ability type determined by said hearing ability type determining unit is the chevron type is to be lower than the suitability when the hearing ability type determined by said hearing ability type determining unit is the high-frequency sloping type, is to be higher than the suitability when the hearing ability type determined by said hearing ability type determining unit is the high-frequency plunging type, and is to be lower than the suitability when the hearing ability type determined by said hearing ability type determining unit is the flat type.

5. The hearing assistance suitability determining device according to claim 1, wherein said hearing ability type determining unit is configured to determine a rate indicating a probability that the hearing ability type of the hearing ability indicated by the hearing ability information corresponds to each of the hearing ability types, and said suitability deciding unit is configured to calculate a multiplication value for each hearing ability type by multiplying a suitability corresponding to a hearing ability type in the table by a rate corresponding to the hearing ability type determined by said hearing ability type determining unit, and to calculate the suitability of the subject for the dichotic hearing assistance by adding up the calculated multiplication values.

6. The hearing assistance suitability determining device according to claim 1, wherein said hearing ability information obtaining unit is configured to obtain, as the hearing ability information, left-ear hearing ability information which indicates a left-ear hearing ability of the subject for frequencies and right-ear hearing ability information which indicates a right-ear hearing ability of the subject for frequencies, and said hearing assistance suitability determining device further comprises:

a hearing ability calculating unit configured to calculate a left-ear high tone hearing ability and a left-ear low tone hearing ability in the left-ear hearing ability information, and a right-ear high tone hearing ability and a right-ear high tone hearing ability in the right-ear hearing ability information, the left-ear high tone hearing ability being a hearing ability in a frequency range higher than a predetermined crossover frequency, the left-ear low tone hearing ability being a hearing ability in a frequency range lower than the crossover frequency, the right-ear high tone hearing ability being a hearing ability in the frequency range higher than the crossover frequency, and the right-ear low tone hearing ability being a hearing ability in the frequency range lower than the crossover frequency;

a first adding unit configured to calculate a right-high-tone hearing ability by adding up the right-ear high tone hearing ability and the left-ear low tone hearing ability;

a second adding unit configured to calculate a left-high-tone hearing ability by adding up the left-ear high tone hearing ability and the right-ear low tone hearing ability; and a high-tone-assignment ear determining unit configured to decide to assign, in the dichotic hearing assistance, an audio signal in a range higher than the crossover frequency to a right ear and an audio signal in a range lower than the crossover frequency to a left ear, when the right-high-tone hearing ability is better than the left-high-tone hearing ability, and to decide to assign, in the dichotic hearing assistance, an audio signal in the range higher than the crossover frequency to the left ear and an audio signal in the range lower than the crossover frequency to the right ear, when the right-high-tone hearing ability is worse than the left-high-tone hearing ability.

7. The hearing assistance suitability determining device according to claim 1, further comprising:

an average hearing ability calculating unit configured to calculate an average hearing ability which is an average value of the hearing ability for the frequencies indicated by the hearing ability information; and a suitability correcting unit configured to decrease the suitability decided by said suitability deciding unit, when the average hearing ability is out of a predetermined range.

8. The hearing assistance suitability determining device according to claim 1, further comprising:

a profile obtaining unit configured to obtain information indicating an age of the subject; and a suitability correcting unit configured to decrease the suitability decided by said suitability deciding unit, when the age of the subject is higher than a predetermined threshold.

9. The hearing assistance suitability determining device according to claim 1, further comprising:

a profile obtaining unit configured to obtain information indicating a period of use which is a period in which the subject has used a hearing aid; and a suitability correcting unit configured to decrease the suitability decided by said suitability deciding unit, when the period of use is less than a predetermined threshold.

10. The hearing assistance suitability determining device according to claim 1, wherein said hearing ability information obtaining unit is configured to obtain, as the hearing ability information, right-ear hearing ability information which indicates a right-ear hearing ability of the subject for frequencies and left-ear hearing ability information which indicates a left-ear hearing ability of the subject for frequencies, and said hearing assistance suitability determining device further comprises:

a binaural difference calculating unit configured to calculate a binaural difference which is a difference between the right-ear hearing ability indicated by the right-ear hearing ability information and the left-ear hearing ability indicated by the left-ear hearing ability information; and a suitability correcting unit configured to decrease the suitability decided by the suitability deciding unit, when the binaural difference is greater than a predetermined threshold.

11. A hearing assistance adjustment system including a hearing aid and a hearing assistance adjustment device which adjusts hearing assistance processing for the hearing aid, wherein said hearing assistance adjustment device includes:

the hearing assistance suitability determining device according to claim 1; and a hearing aid setting unit configured to adjust the hearing assistance processing for the hearing aid, based on a suitability of a subject for dichotic hearing assistance determined by the hearing assistance suitability determining device.

12. A semiconductor integrated circuit which determines a suitability of a subject for dichotic hearing assistance, said semiconductor integrated circuit comprising:

a hearing ability information obtaining unit configured to obtain hearing ability information indicating a hearing ability of the subject for frequencies;

a hearing ability type determining unit configured to determine, among hearing ability types each of which is defined by a tendency in a change of the hearing ability with respect to the frequencies, a hearing ability type of the hearing ability indicated by the hearing ability information; and a suitability deciding unit configured to decide, with reference to a table, the suitability of the subject for the dichotic hearing assistance based on a suitability corresponding, in the table, to the hearing ability type determined by said hearing ability type determining unit, the table showing a correspondence relationship between each of the hearing ability types and one of suitabilities for dichotic hearing assistance, wherein one of the hearing ability types is a high-frequency sloping type in which a hearing ability decreases as a frequency becomes higher, and said suitability deciding unit is configured to decide that the suitability of the subject for the dichotic hearing assistance when the hearing ability type determined by said hearing ability type determining unit is the high-frequency sloping type is to be higher than the suitability when the hearing ability type determined by said hearing ability type determining unit is not the high-frequency sloping type.

13. A hearing assistance suitability determining method for determining a suitability of a subject for dichotic hearing assistance, said hearing assistance suitability determining method comprising:

obtaining hearing ability information indicating a hearing ability of the subject for frequencies;

determining, among hearing ability types each of which is defined by a tendency in a change of the hearing ability with respect to the frequencies, a hearing ability type of the hearing ability indicated by the hearing ability information; and deciding, with reference to a table, the suitability of the subject for the dichotic hearing assistance based on a suitability corresponding, in the table, to the hearing ability type determined in said determining, the table showing a correspondence relationship between each of the hearing ability types and one of suitabilities for dichotic hearing assistance, wherein one of the hearing ability types is a high-frequency sloping type in which a hearing ability decreases as a frequency becomes higher, and in said deciding, it is decided that the suitability of the subject for the dichotic hearing assistance when the hearing ability type determined in said determining is the high-frequency sloping type is to be higher than the suitability when the hearing ability type determined in said determining is not the high-frequency sloping type.

* * * * *